(12) United States Patent
Terao et al.

(10) Patent No.: US 12,372,517 B2
(45) Date of Patent: Jul. 29, 2025

(54) METHOD FOR SEPARATING ANTIBODY, AND METHOD FOR TESTING ON DISEASE

(71) Applicant: TOSOH CORPORATION, Yamaguchi (JP)

(72) Inventors: Yosuke Terao, Kanagawa (JP); Yasuyuki Akiyama, Kanagawa (JP); Satoshi Endo, Kanagawa (JP); Ryoko Watanabe, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 1239 days.

(21) Appl. No.: 17/253,824

(22) PCT Filed: Jun. 18, 2019

(86) PCT No.: PCT/JP2019/024160
§ 371 (c)(1),
(2) Date: Dec. 18, 2020

(87) PCT Pub. No.: WO2019/244901
PCT Pub. Date: Dec. 26, 2019

(65) Prior Publication Data
US 2021/0116445 A1 Apr. 22, 2021

(30) Foreign Application Priority Data

Jun. 20, 2018 (JP) .................... 2018-116611
Jan. 31, 2019 (JP) .................... 2019-015596

(51) Int. Cl.
*G01N 33/538* (2006.01)
*G01N 33/543* (2006.01)

(52) U.S. Cl.
CPC ......... *G01N 33/538* (2013.01); *G01N 33/543* (2013.01); *G01N 2800/50* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 2009/0186371 A1 | 7/2009 | Miyoshi et al. | |
| 2017/0218044 A1 | 8/2017 | Asaoka et al. | |
| 2017/0313767 A1 | 11/2017 | Alter et al. | |
| 2018/0059094 A1 | 3/2018 | Nishikaze | |
| 2019/0211077 A2 | 7/2019 | Asaoka et al. | |

FOREIGN PATENT DOCUMENTS

| | | |
|---|---|---|
| JP | 2015-522260 A | 8/2015 |
| JP | 2016-099304 A | 5/2016 |
| JP | 2016-108294 A | 6/2016 |
| JP | 2016-194500 A | 11/2016 |
| JP | 2018-011515 A | 1/2018 |
| JP | 2021-162586 A | 10/2021 |
| WO | 00/61636 A2 | 10/2000 |
| WO | 2006/114661 A1 | 11/2006 |
| WO | WO-2007136001 A1 * | 11/2007 ......... G01N 33/6854 |
| WO | 2013/120929 A1 | 8/2013 |
| WO | 2013/188846 A1 | 12/2013 |
| WO | WO-2015199154 A1 * | 12/2015 ......... B01D 15/3809 |

OTHER PUBLICATIONS

Partial supplementary European Search Report dated Mar. 24, 2022 issued in corresponding European Application No. 19822237.4.
M. Kiyoshi et al., Scientific Reports, vol. 8, No. 3955, 2018, pp. 1-11.
Office Action issued in corresponding Chinese application No. 201980040776.7 dated Oct. 26, 2022, along with English translation thereof.
"Glycan analysis of human IgG using Palstation TM", Takara Bio catalog, Takara Bio Inc. <http://catalog.takara-bio.co.jp/product/basic_info.php?unitid=U100002765&recommend_flg=1&click_flg=1>, Sep. 2, 2019.
Anthony et al., "A Recombinant IgG Fc That Recapitulates the Anti-Inflammatory Activity of IVIG", Science, vol. 320, Issue 5874, 2008, pp. 373-376.
Jefferis, "Glycoforms of Human IgG in Health and Disease", Trends in Glycoscience and Glycotechnology, vol. 21, No. 118, 2009, pp. 105-117.
Terao et al., "Separation of Antibody by Fc Receptor Resin Based on Antibody's Glycan Structures", Tosoh Research & Technology Review, vol. 61, 2017, pp. 33-41.
Ohmi et al., "Sialylation converts arthritogenic IgG into inhibitors of collagen-induced arthritis", Nature Communications, vol. 7, No. 11205, 2016, p. 12.

(Continued)

*Primary Examiner* — Sharon X Wen
(74) *Attorney, Agent, or Firm* — Greenblum & Bernstein, P.L.C.

(57) ABSTRACT

An object of the present invention is to provide a method for detecting the presence or absence of a disease, the risk of developing a disease, the degree of progression of a disease and/or the degree of progression of aging, in a subject. The present invention achieves the above described object by a method including the following steps (a) to (c): (a) adding a solution containing an antibody obtained from a subject to a column filled with an insoluble carrier on which an Fc-binding protein is immobilized, to allow the antibody to be adsorbed on the carrier; (b) eluting the antibody adsorbed on the carrier using an eluent, to obtain data of a separation pattern of the antibody; and (c) detecting the presence or absence of a disease, the risk of developing a disease, the degree of progression of a disease and/or the degree of progression of aging, in the subject, using the data as an indicator.

14 Claims, 12 Drawing Sheets
Specification includes a Sequence Listing.

(56) References Cited

OTHER PUBLICATIONS

Yagi et al., "Characterization of Oligosaccharides in Therapeutic Antibodies", Chromatography, vol. 34, No. 2, 2013, pp. 83-88.
International Search Report issued in International Patent Application No. PCT/JP2019/024160, dated Sep. 17, 2019, along with an English translation thereof.
Written Opinion of the International Searching Authority issued in International Patent Application No. PCT/JP2019/024160, dated Sep. 17, 2019, along with an English translation thereof.

* cited by examiner

[Fig. 1]
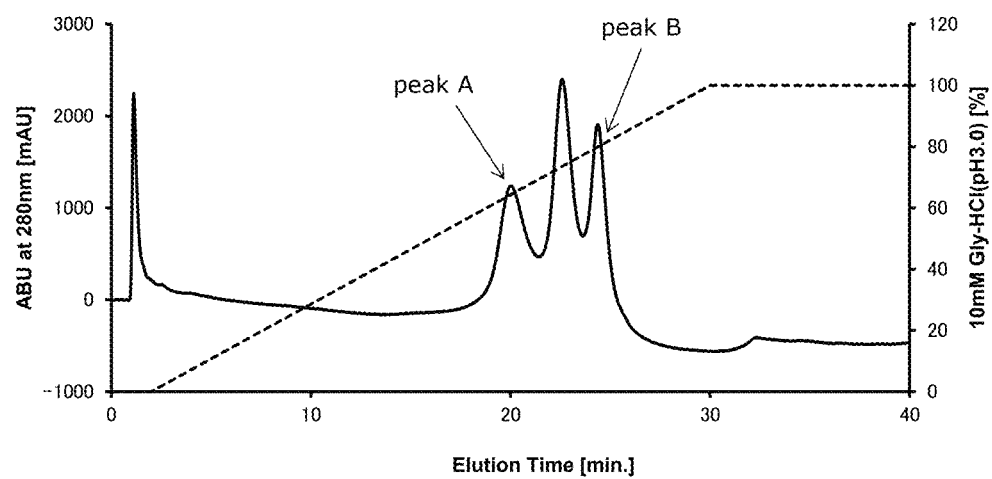

[Fig. 2]
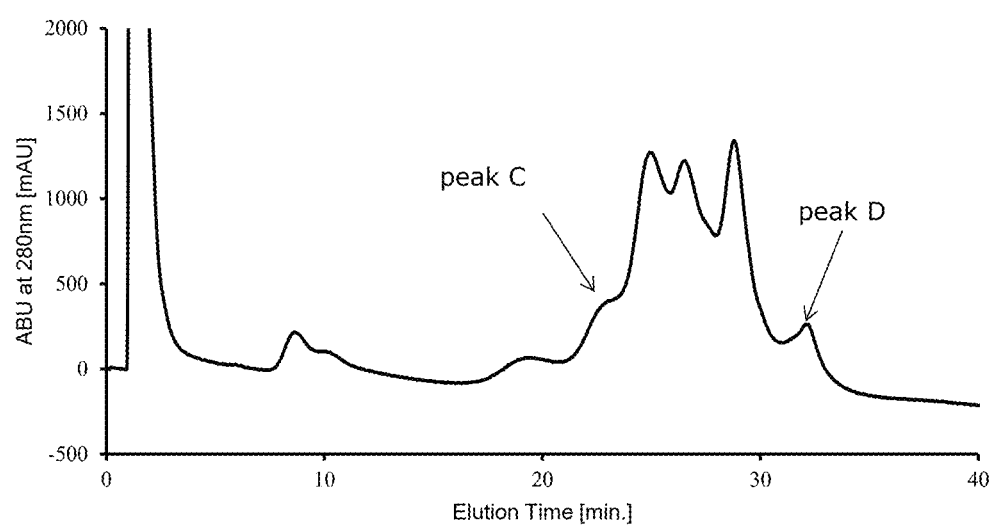

[Fig. 3]

| ABBREVIATION | SUGAR CHAIN STRUCTURE |
|---|---|
| Man5 | Manα1\6<br>　　　3Manα1\<br>Manα1　　　　6Manβ1-4GlcNAcβ1-4GlcNAc<br>　　　　　　　3<br>　　　Manα1 |
| G0 | GlcNAcβ1-2Manα1\<br>　　　　　　　　　6Manβ1-4GlcNAcβ1-4GlcNAc<br>　　　　　　　　　3<br>GlcNAcβ1-2Manα1 |
| G0F | GlcNAcβ1-2Manα1\　　　　Fucα1\6<br>　　　　　　　　　6Manβ1-4GlcNAcβ1-4GlcNAc<br>　　　　　　　　　3<br>GlcNAcβ1-2Manα1 |
| G1Fa | Galβ1-4GlcNAcβ1-2Manα1\　　Fucα1\6<br>　　　　　　　　　　　6Manβ1-4GlcNAcβ1-4GlcNAc<br>　　　　　　　　　　　3<br>　　　　GlcNAcβ1-2Manα1 |
| G1Fb | GlcNAcβ1-2Manα1\　　　　　Fucα1\6<br>　　　　　　　　　6Manβ1-4GlcNAcβ1-4GlcNAc<br>　　　　　　　　　3<br>Galβ1-4GlcNAcβ1-2Manα1 |
| G2F | Galβ1-4GlcNAcβ1-2Manα1\　　Fucα1\6<br>　　　　　　　　　　　6Manβ1-4GlcNAcβ1-4GlcNAc<br>　　　　　　　　　　　3<br>Galβ1-4GlcNAcβ1-2Manα1 |
| G1F+SA | GlcNAcβ1-2Manα1\　　　　　　Fucα1\6<br>　　　　　　　　　　　6Manβ1-4GlcNAcβ1-4GlcNAc<br>　　　　　　　　　　　3<br>NeuAc-Galβ1-4GlcNAcβ1-2Manα1 |
| G2F+SA | Galβ1-4GlcNAcβ1-2Manα1\　　　Fucα1\6<br>　　　　　　　　　　　　6Manβ1-4GlcNAcβ1-4GlcNAc<br>　　　　　　　　　　　　3<br>NeuAc-Galβ1-4GlcNAcβ1-2Manα1 |
| G2F+2SA | NeuAc-Galβ1-4GlcNAcβ1-2Manα1\　Fucα1\6<br>　　　　　　　　　　　　　6Manβ1-4GlcNAcβ1-4GlcNAc<br>　　　　　　　　　　　　　3<br>NeuAc-Galβ1-4GlcNAcβ1-2Manα1 |

[Fig. 4]

| ABBREVIATION | SUGAR CHAIN STRUCTURE | ABBREVIATION | SUGAR CHAIN STRUCTURE |
|---|---|---|---|
| G0 | GlcNAcβ1-2Manα1\\$_3^6$Manβ1-4GlcNAcβ1-4GlcNAc / GlcNAcβ1-2Manα1 | G1F+SA | NeuAc,Gal,[GlcNAcβ1-2Manα1 / GlcNAcβ1-2Manα1] Fucα1\\$_3^6$Manβ1-4GlcNAcβ1-4GlcNAc |
| G0F | GlcNAcβ1-2Manα1\\ Fucα1\\$_3^6$Manβ1-4GlcNAcβ1-4GlcNAc / GlcNAcβ1-2Manα1 | G2F+SA | NeuAc₁[Galβ1-4GlcNAcβ1-2Manα1 / Galβ1-4GlcNAcβ1-2Manα1] Fucα1\\$_3^6$Manβ1-4GlcNAcβ1-4GlcNAc |
| G1 | Gal₁[GlcNAcβ1-2Manα1 / GlcNAcβ1-2Manα1]$_3^6$Manβ1-4GlcNAcβ1-4GlcNAc | G2F+2SA | NeuAc-Galβ1-4GlcNAcβ1-2Manα1\\ Fucα1\\$_3^6$Manβ1-4GlcNAcβ1-4GlcNAc / NeuAc-Galβ1-4GlcNAcβ1-2Manα1 |
| G0F+GN | GlcNAcβ1-2Manα1\\ Fucα1\\ GlcNAcβ1-4$_3^6$Manβ1-4GlcNAcβ1-4GlcNAc / GlcNAcβ1-2Manα1 | G2F+GN | Galβ1-4GlcNAcβ1-2Manα1\\ Fucα1\\ GlcNAcβ1-4$_3^6$Manβ1-4GlcNAcβ1-4GlcNAc / Galβ1-4GlcNAcβ1-2Manα1 |
| G1Fa | Galβ1-4GlcNAcβ1-2Manα1\\ Fucα1\\$_3^6$Manβ1-4GlcNAcβ1-4GlcNAc / GlcNAcβ1-2Manα1 | S1 | NeuAc,Gal,GlcNAc,[GlcNAcβ1-2Manα1 / GlcNAcβ1-2Manα1] Fucα1\\$_3^6$Manβ1-4GlcNAcβ1-4GlcNAc |
| G1Fb | GlcNAcβ1-2Manα1\\ Fucα1\\$_3^6$Manβ1-4GlcNAcβ1-4GlcNAc / Galβ1-4GlcNAcβ1-2Manα1 | S2 | NeuAc,GlcNAc,[Galβ1-4GlcNAcβ1-2Manα1 / Galβ1-4GlcNAcβ1-2Manα1] Fucα1\\$_3^6$Manβ1-4GlcNAcβ1-4GlcNAc |
| G1F+GN | Gal,GlcNAc,[GlcNAcβ1-2Manα1 / GlcNAcβ1-2Manα1] Fucα1\\$_3^6$Manβ1-4GlcNAcβ1-4GlcNAc | S3 | GlcNAc,[NeuAc-Galβ1-4GlcNAcβ1-2Manα1 / NeuAc-Galβ1-4GlcNAcβ1-2Manα1] Fucα1\\$_3^6$Manβ1-4GlcNAcβ1-4GlcNAc |
| G2 | Galβ1-4GlcNAcβ1-2Manα1\\$_3^6$Manβ1-4GlcNAcβ1-4GlcNAc / Galβ1-4GlcNAcβ1-2Manα1 | G2+SA | NeuAc,[Galβ1-4GlcNAcβ1-2Manα1 / Galβ1-4GlcNAcβ1-2Manα1]$_3^6$Manβ1-4GlcNAcβ1-4GlcNAc |
| G2F | Galβ1-4GlcNAcβ1-2Manα1\\ Fucα1\\$_3^6$Manβ1-4GlcNAcβ1-4GlcNAc / Galβ1-4GlcNAcβ1-2Manα1 | G2+2SA | NeuAc-Galβ1-4GlcNAcβ1-2Manα1\\$_3^6$Manβ1-4GlcNAcβ1-4GlcNAc / NeuAc-Galβ1-4GlcNAcβ1-2Manα1 |

[Fig. 5]
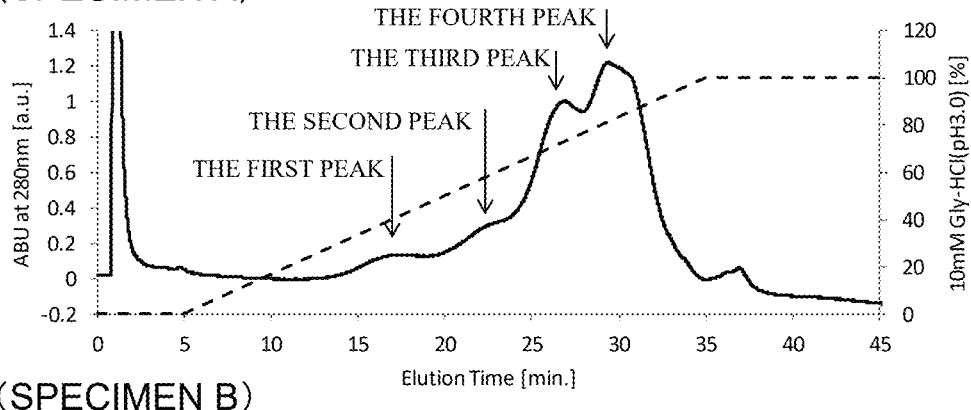
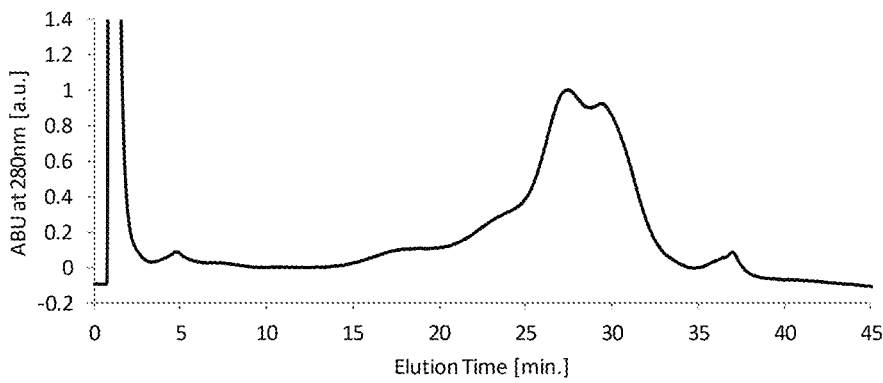
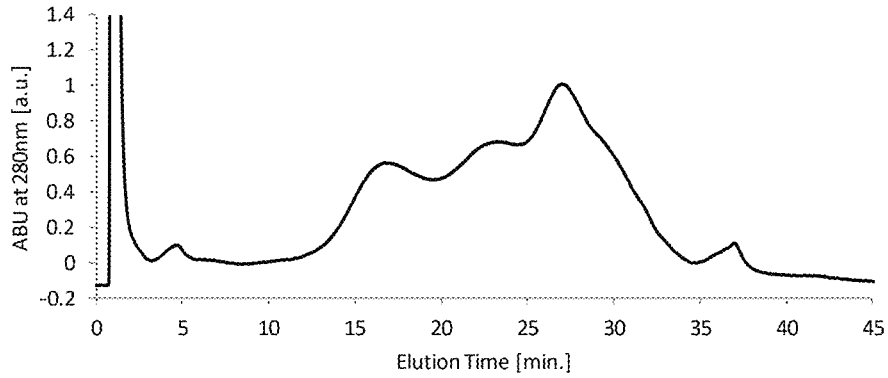

[Fig. 6]
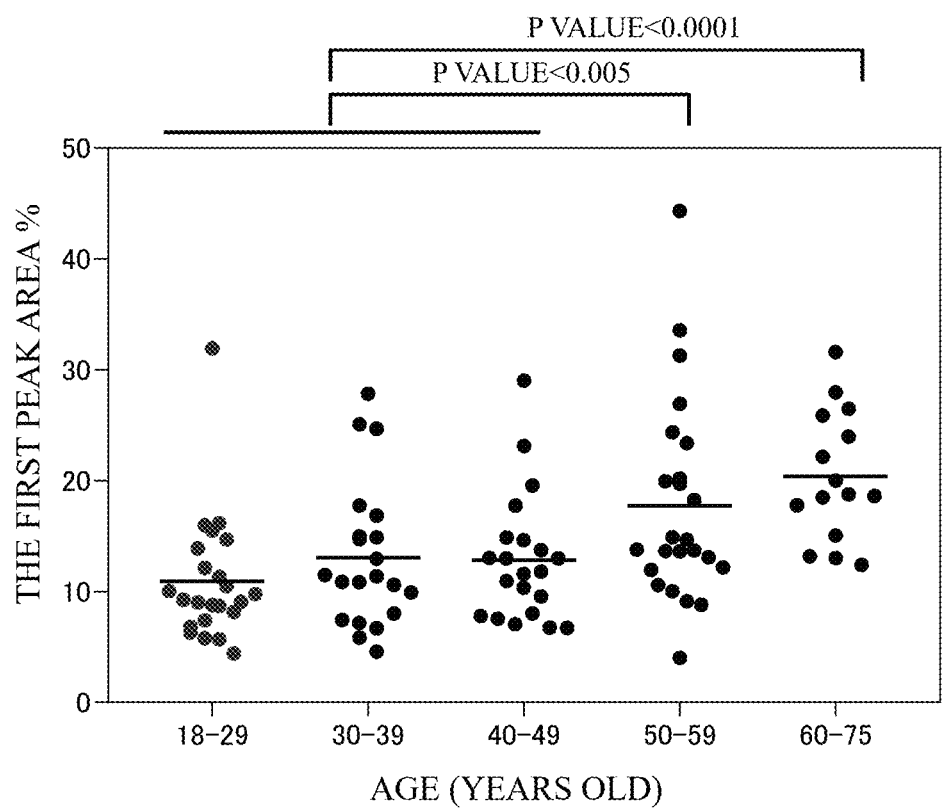

[Fig. 7]
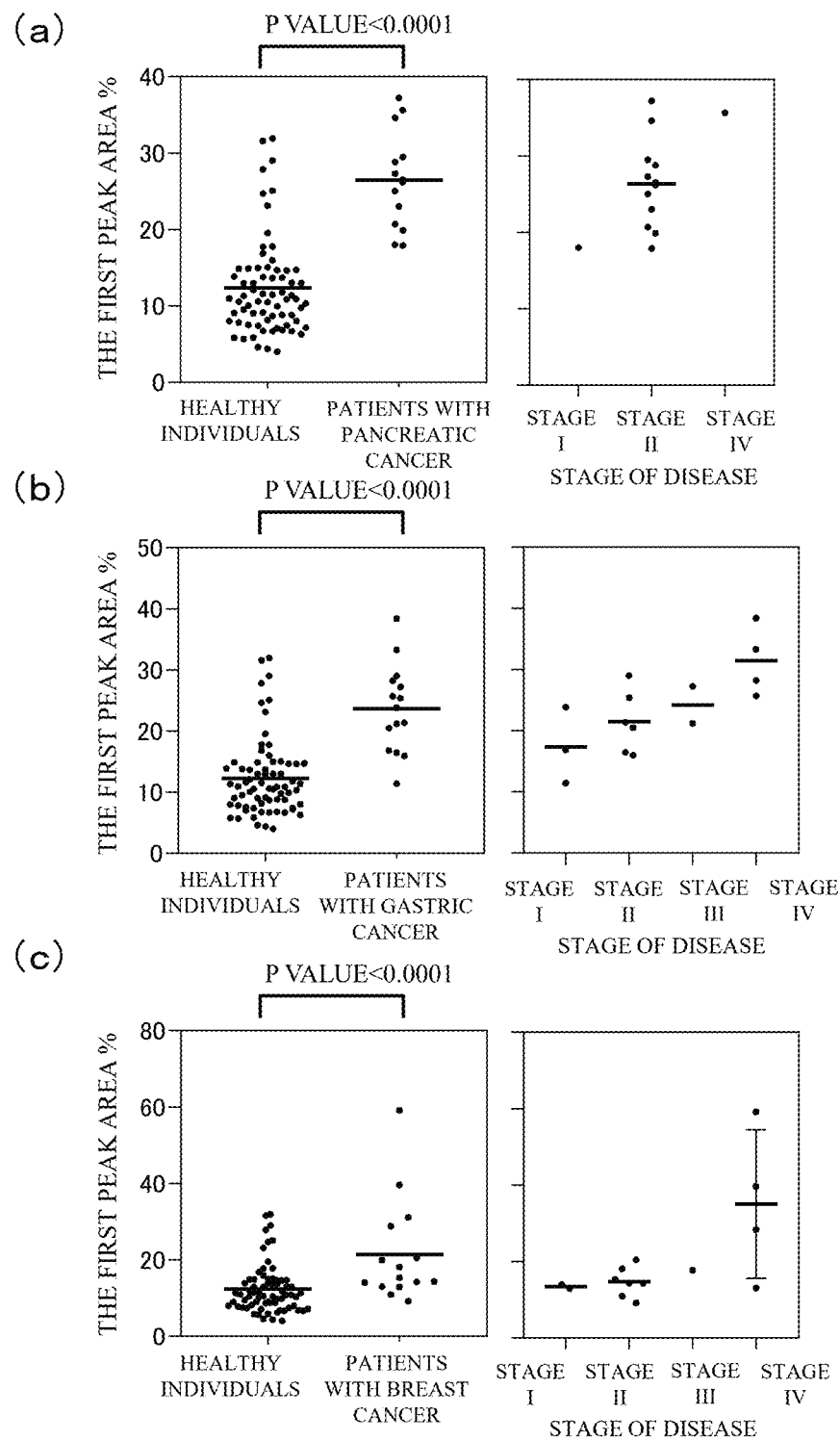

[Fig. 8]
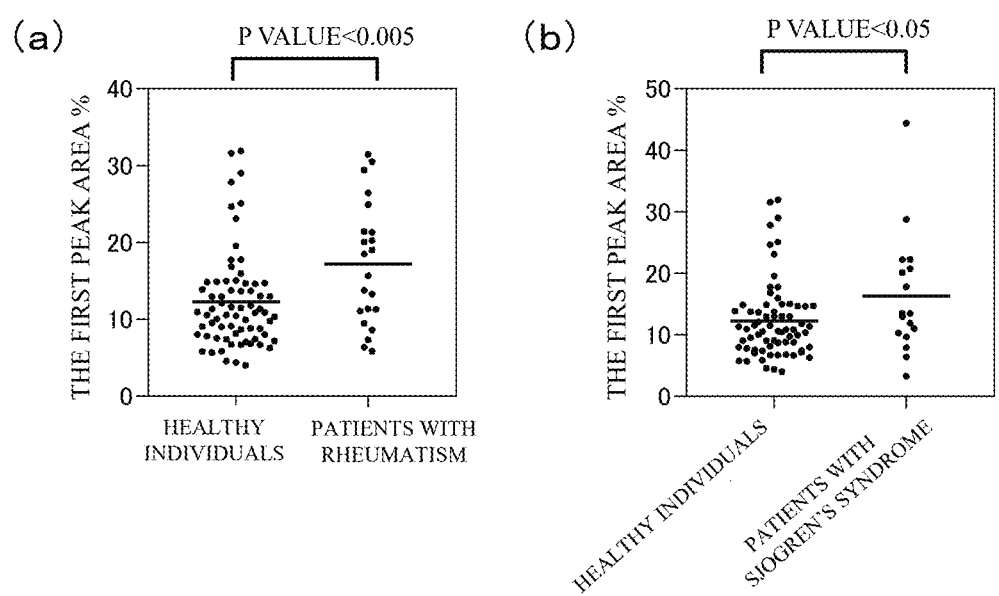

[Fig. 9]
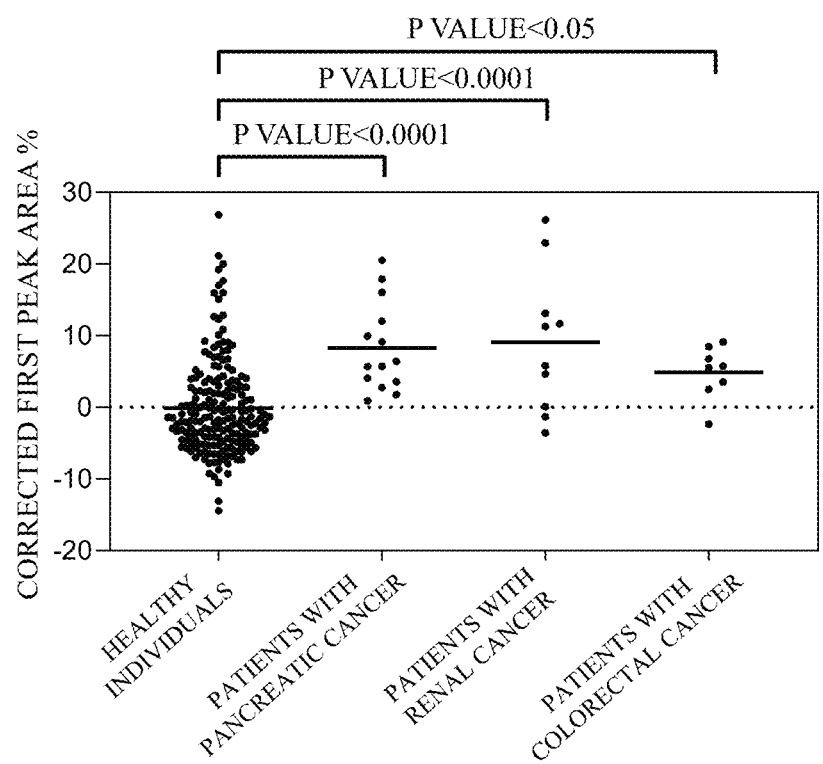

[Fig. 10]
(a)
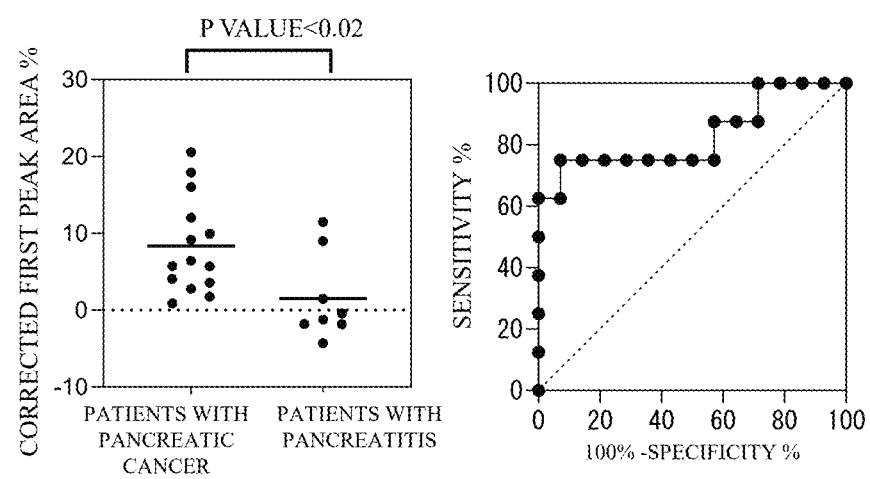
(b)
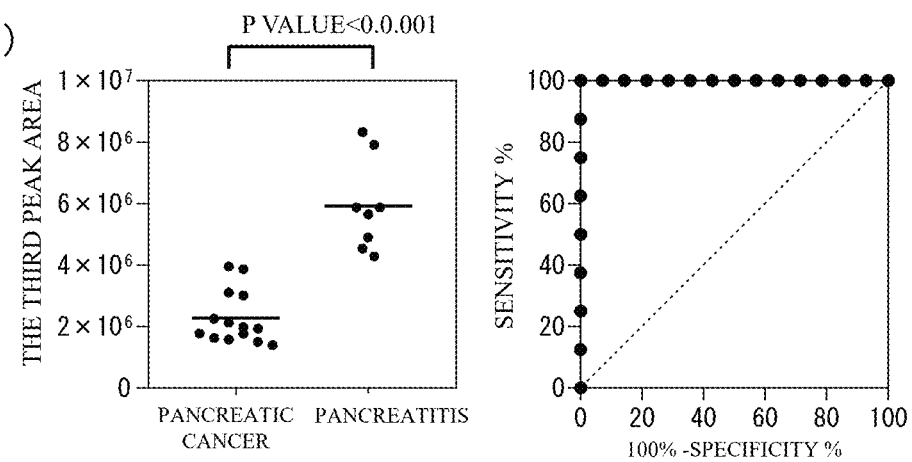

[Fig. 11]
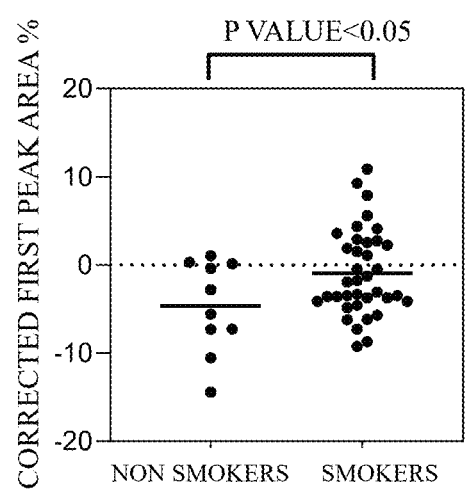

[Fig. 12]
(a)
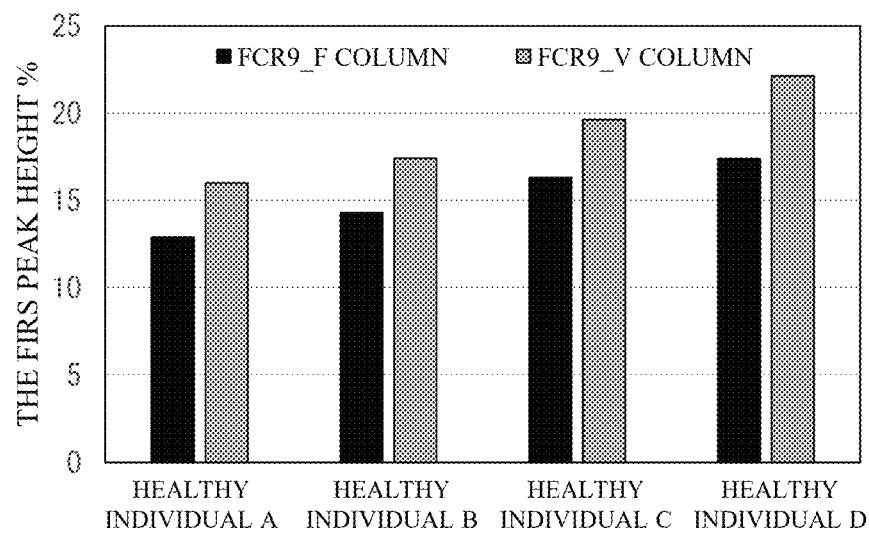
(b)
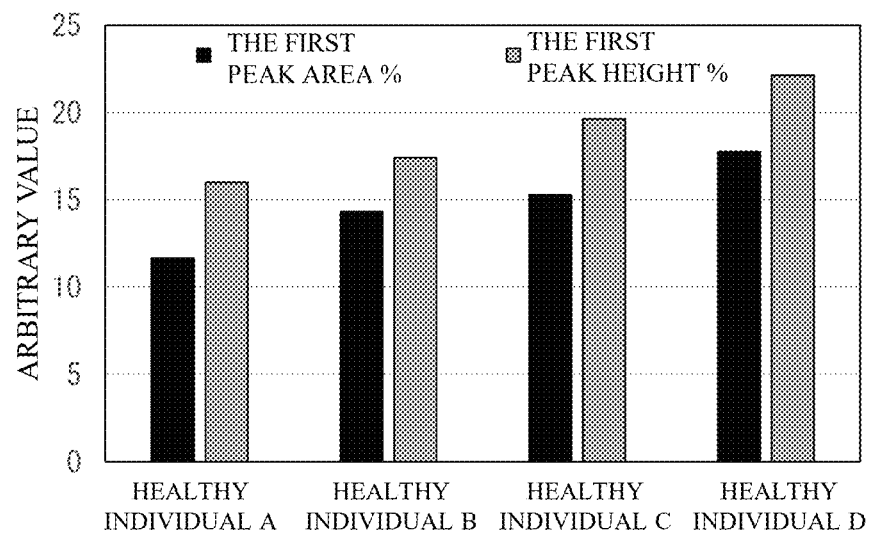

SEQUENCE LISTING

<160> NUMBER OF SEQ ID NOS: 18

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
            165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
            245                 250

<210> SEQ ID NO 2
<211> LENGTH: 216
<212> TYPE: PRT
<213> ORGANISM: Artificial sequence
<220> FEATURE:
<223> OTHER INFORMATION: FcR9

<400> SEQUENCE: 2

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
            35                  40                  45

Gln Trp Asn Arg Val Leu Glu Lys Asp Ser Val Thr Leu Lys Cys Arg
            50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
            85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
        210                 215

<210> SEQ ID NO 3
<211> LENGTH: 648
<212> TYPE: DNA
<213> ORGANISM: Artificial sequence
<220> FEATURE:
<223> OTHER INFORMATION: Polynucleotide encoding FcR9

<400> SEQUENCE: 3
atgaaaataa aaacaggtgc acgcatcctc gcattatccg cattaacgac gatgatgttt    60
tccgcctcgg ctctcgccaa aatcgaagaa gccatgggca tgcgtaccga agatctgccg   120
aaagcggagg tgattctgga accgcagtgg aatcgcgtgc tggagaaaga ttctgtgacc   180
cttaaatgcc ggggcgcgta tagcccggaa gataacagca cccagtggtt ccacaatgaa   240
agcctgattt ccagccaggc gagcagctac cttattgatg cggcgacggt ggatgatagc   300
ggcgaatatc gttgccagac cagcctgagc accctgagcg atccggtgca gctggaggtg   360
cacatcgggt ggcttctgtt acaggctcca cggtgggagt tcaaagaggg ggatccgatt   420
catctgcggt gtcactcctg gaagaatacc gccctgcata agtgacctac cctgcaaaac   480
ggcaagggcc gcaagtattt ccaccacaac tccgacttct atattcccaa agcgacgctg   540
aaggacagcg gcagctattc ctgccgtggg ctggtgggcg caaaaatgt gagcagcgag    600 accgtgaata ttaccattac ccaaggggc catcatcatc atcatcat               648

<210> SEQ ID NO 4
<211> LENGTH: 216
<212> TYPE: PRT
<213> ORGANISM: Artificial sequence
<220> FEATURE:
<223> OTHER INFORMATION: MalE-CD16a-6His

<400> SEQUENCE: 4

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Val Val Phe Leu Glu Pro
            35                  40                  45

Gln Trp Tyr Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Phe Ile Asp Ala Ala Thr 85                  90                  95
Val Asp Asp Ser Gly Glu Tyr Arg Cys Gln Thr Asn Leu Ser Thr Leu
                100                 105                 110

Ser Asp Pro Val Gln Leu Glu Val His Ile Gly Trp Leu Leu Leu Gln
            115                 120                 125

Ala Pro Arg Trp Val Phe Lys Glu Glu Asp Pro Ile His Leu Arg Cys
        130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 5
<211> LENGTH: 20
<212> TYPE: DNA
<213> ORGANISM: Artificial sequence
<220> FEATURE:
<223> OTHER INFORMATION: Oligonucleotide

<400> SEQUENCE: 5
taatacgact cactataggg                                             20

<210> SEQ ID NO 6
<211> LENGTH: 30
<212> TYPE: DNA
<213> ORGANISM: Artificial sequence
<220> FEATURE:
<223> OTHER INFORMATION: Oligonucleotide

<400> SEQUENCE: 6 cattttgct gccgaacagc ccacggcagg                                   30

<210> SEQ ID NO 7
<211> LENGTH: 19
<212> TYPE: DNA
<213> ORGANISM: Artificial sequence
<220> FEATURE:
<223> OTHER INFORMATION: Oligonucleotide

<400> SEQUENCE: 7
tatgctagtt attgctcag                                              19

<210> SEQ ID NO 8
<211> LENGTH: 30
<212> TYPE: DNA
<213> ORGANISM: Artificial sequence
<220> FEATURE:
<223> OTHER INFORMATION: Oligonucleotide

<400> SEQUENCE: 8
cctgccgtgg gctgttcggc agcaaaaatg                                  30

<210> SEQ ID NO 9
<211> LENGTH: 216
<212> TYPE: PRT
<213> ORGANISM: Artificial sequence
<220> FEATURE:
<223> OTHER INFORMATION: FcR9_F

<400> SEQUENCE: 9

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Phe
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 10
<211> LENGTH: 648
<212> TYPE: DNA
<213> ORGANISM: Artificial sequence
<220> FEATURE:
<223> OTHER INFORMATION: Polynucleotide encoding FcR9_F

<400> SEQUENCE: 10
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata agtgacctac ctgcaaaac     480 ggcaagggcc gcaagtattt ccaccacaac tccgacttct atattcccaa agcgacgctg     540
aaggacagcg gcagctattc ctgccgtggg ctgttcggca gcaaaaatgt gagcagcgag     600
accgtgaata ttaccattac ccaagggggc catcatcatc atcatcat                  648

```
<210> SEQ ID NO 11
<211> LENGTH: 37
<212> TYPE: DNA
<213> ORGANISM: Artificial sequence
<220> FEATURE:
<223> OTHER INFORMATION: Oligonucleotide

<400> SEQUENCE: 11
tagccatggg catgcgtacc gaagatctgc cgaaagc                              37

<210> SEQ ID NO 12
<211> LENGTH: 66
<212> TYPE: DNA
<213> ORGANISM: Artificial sequence
<220> FEATURE:
<223> OTHER INFORMATION: Oligonucleotide

<400> SEQUENCE: 12
cccaagctta tccgcaggta tcgttgcggc acccttgggt aatggtaata ttcacggtct    60
cgctgc                                                                66

<210> SEQ ID NO 13
<211> LENGTH: 19
<212> TYPE: DNA
<213> ORGANISM: Artificial sequence
<220> FEATURE:
<223> OTHER INFORMATION: Oligonucleotide

<400> SEQUENCE: 13
tgtggtatgg ctgtgcagg                                                  19

<210> SEQ ID NO 14
<211> LENGTH: 18
<212> TYPE: DNA
<213> ORGANISM: Artificial sequence
<220> FEATURE:
<223> OTHER INFORMATION: Oligonucleotide

<400> SEQUENCE: 14
tcggcatggg gtcaggtg                                                   18

<210> SEQ ID NO 15
<211> LENGTH: 207
<212> TYPE: PRT
<213> ORGANISM: Artificial sequence
<220> FEATURE:
<223> OTHER INFORMATION: FcR9_F_Cys

<400> SEQUENCE: 15

Met Lys Tyr Leu Leu Ser Thr Ala Ala Ala Gly Leu Leu Leu Leu Ala
1               5                   10                  15

Ala Gln Pro Ala Met Ala Met Gly Met Arg Thr Glu Asp Leu Pro Lys
            20                  25                  30

Ala Glu Val Ile Leu Glu Pro Gln Trp Asn Arg Val Leu Glu Lys Asp
        35                  40                  45

Ser Val Thr Leu Lys Cys Arg Gly Ala Tyr Ser Pro Glu Asp Asn Ser
    50                  55                  60

Thr Gln Trp Phe His Asn Glu Ser Leu Ile Ser Ser Gln Ala Ser Ser
65                  70                  75                  80

Tyr Leu Ile Asp Ala Ala Thr Val Asp Asp Ser Gly Glu Tyr Arg Cys
                85                  90                  95

Gln Thr Ser Leu Ser Thr Leu Ser Asp Pro Val Gln Leu Glu Val His
```

Ile Gly Trp Leu Leu Leu Gln Ala Pro Arg Trp Glu Phe Lys Glu Gly
                115                 120                 125

Asp Pro Ile His Leu Arg Cys His Ser Trp Lys Asn Thr Ala Leu His
            130                 135                 140

Lys Val Thr Tyr Leu Gln Asn Gly Lys Gly Arg Lys Tyr Phe His His
145                 150                 155                 160

Asn Ser Asp Phe Tyr Ile Pro Lys Ala Thr Leu Lys Asp Ser Gly Ser
                165                 170                 175

Tyr Ser Cys Arg Gly Leu Phe Gly Ser Lys Asn Val Ser Ser Glu Thr
            180                 185                 190

Val Asn Ile Thr Ile Thr Gln Gly Cys Arg Asn Asp Thr Cys Gly
                195                 200                 205

<210> SEQ ID NO 16
<211> LENGTH: 621
<212> TYPE: DNA
<213> ORGANISM: Artificial sequence
<220> FEATURE:
<223> OTHER INFORMATION: Polynucleotide encoding FcR9_F_Cys

<400> SEQUENCE: 16
atgaaatacc tgctgtcgac cgctgctgct ggtctgctgc tcctcgctgc ccagccggcg      60
atggccatgg gcatgcgtac cgaagatctg ccgaaagcgg aggtgattct ggaaccgcag     120
tggaatcgcg tgctggagaa agattctgtg acccttaaat gccggggcgc gtatagcccg     180
gaagataaca gcacccagtg gttccacaat gaaagcctga tttccagcca ggcgagcagc     240
taccttattg atgcggcgac ggtggatgat agcggcgaat atcgttgcca gaccagcctg     300 agcacccctga cgatccggt gcagctggag gtgcacatcg gtggcttcct gttacaggct     360
ccacggtggg agttcaaaga gggggatccg attcatctgc ggtgtcactc ctggaagaat     420
accgccctgc ataaagtgac ctacctgcaa aacggcaagg gccgcaagta tttccaccac     480
aactccgact ctatattcc caaagcgacg ctgaaggaca gcggcagcta ttcctgccgt     540
gggctgttcg gcagcaaaaa tgtgagcagc gagaccgtga atattaccat tacccaaggg     600
tgccgcaacg atacttgcgg a                                              621

<210> SEQ ID NO 17
<211> LENGTH: 207
<212> TYPE: PRT
<213> ORGANISM: Artificial sequence
<220> FEATURE:
<223> OTHER INFORMATION: FcR9_V_Cys

<400> SEQUENCE: 17

Met Lys Tyr Leu Leu Ser Thr Ala Ala Ala Gly Leu Leu Leu Leu Ala
1               5                   10                  15

Ala Gln Pro Ala Met Ala Met Gly Met Arg Thr Glu Asp Leu Pro Lys
            20                  25                  30

Ala Glu Val Ile Leu Glu Pro Gln Trp Asn Arg Val Leu Glu Lys Asp
        35                  40                  45

Ser Val Thr Leu Lys Cys Arg Gly Ala Tyr Ser Pro Glu Asp Asn Ser
    50                  55                  60

Thr Gln Trp Phe His Asn Glu Ser Leu Ile Ser Ser Gln Ala Ser Ser
65                  70                  75                  80

Tyr Leu Ile Asp Ala Ala Thr Val Asp Asp Ser Gly Glu Tyr Arg Cys
                85                  90                  95

-continued

```
Gln Thr Ser Leu Ser Thr Leu Ser Asp Pro Val Gln Leu Glu Val His
            100                 105                 110

Ile Gly Trp Leu Leu Leu Gln Ala Pro Arg Trp Glu Phe Lys Glu Gly
            115                 120                 125

Asp Pro Ile His Leu Arg Cys His Ser Trp Lys Asn Thr Ala Leu His
            130                 135                 140

Lys Val Thr Tyr Leu Gln Asn Gly Lys Gly Arg Lys Tyr Phe His His
145                 150                 155                 160

Asn Ser Asp Phe Tyr Ile Pro Lys Ala Thr Leu Lys Asp Ser Gly Ser
                165                 170                 175

Tyr Ser Cys Arg Gly Leu Val Gly Ser Lys Asn Val Ser Ser Glu Thr
            180                 185                 190

Val Asn Ile Thr Ile Thr Gln Gly Cys Arg Asn Asp Thr Cys Gly
            195                 200                 205

<210> SEQ ID NO 18
<211> LENGTH: 621
<212> TYPE: DNA
<213> ORGANISM: Artificial sequence
<220> FEATURE:
<223> OTHER INFORMATION: Polynucleotide encoding FcR9_V_Cys

<400> SEQUENCE: 18
atgaaatacc tgctgtcgac cgctgctgct ggtctgctgc tcctcgctgc ccagccggcg      60
atggccatgg gcatgcgtac cgaagatctg ccgaaagcgg aggtgattct ggaaccgcag     120
tggaatcgcg tgctggagaa agattctgtg acccttaaat gccggggcgc gtatagcccg     180
gaagataaca gcacccagtg gttccacaat gaaagcctga tttccagcca ggcgagcagc     240
taccttattg atgcggcgac ggtggatgat agcggcgaat atcgttgcca gaccagcctg     300
agcaccctga gcgatccggt gcagctggag gtgcacatcg ggtggcttct gttacaggct     360
ccacggtggg agttcaaaga gggggatccg attcatctgc ggtgtcactc ctggaagaat     420
accgccctgc ataaagtgac ctacctgcaa aacggcaagg gccgcaagta tttccaccac     480
aactccgact tctatattcc caaagcgacg ctgaaggaca gcggcagcta ttcctgccgt     540
gggctggtgg gcagcaaaaa tgtgagcagc gagaccgtga atattaccat tacccaaggg     600
tgccgcaacg atacttgcgg a                                              621
```

METHOD FOR SEPARATING ANTIBODY, AND METHOD FOR TESTING ON DISEASE

TECHNICAL FIELD

The present invention relates to a method for separating an antibody, and the use thereof. Specifically, for example, the present invention relates to a method for detecting the presence or absence of a disease, the risk of developing a disease, the degree of progression of a disease and/or the degree of progression of aging, in a subject, using as an indicator(s), a characteristic(s) of a separation pattern upon separating an antibody obtained from the subject.

BACKGROUND ART

In recent years, pharmaceutical drugs containing antibodies (namely, antibody drugs) are used in the treatment of cancer, immune diseases and the like. Antibodies to be used in antibody drugs are produced by culturing cells (such as Chinese hamster ovary (CHO) cells) which are obtained by genetic engineering techniques and capable of expressing the antibodies, and then purifying the antibodies to a high-purity using column chromatography or the like. However, recent studies have revealed that the antibodies produced as described above exist in the form of assemblies of various molecules, as a result of being subjected to modifications such as oxidation, reduction, isomerization and glycosylation, and impacts on drug efficacy and safety are concerned. In particular, the structures of sugar chains bound to antibodies have been reported to have a great impact on the activity, dynamics and safety of the resulting antibody drugs, and it is thus important to analyze such sugar chain structures in detail (Non-patent Document 1). Further, in a disease such as rheumatism, changes in the sugar chain structures added to antibodies in blood are known (Non-patent Documents 2 and 3), and there are possibilities that the analysis of the sugar chain structures added to the antibodies enables the diagnosis of such a disease.

An LC-MS analysis including cleavage of sugar chains has been mainly performed, as a method for analyzing the sugar chain structures of an antibody to be used in an antibody drug (Patent Document 1 and Patent Document 2). However, the above described analysis method involves extremely complicated operations and requires an enormous period of time. A simpler method for analyzing the molecular structure of an antibody may be, for example, an analysis by chromatography. Specifically, it is possible to separate and quantify agglomerates and degradation products by separating an antibody based on molecular weight, using gel filtration chromatography. Further, it is possible to separate an antibody based on the difference in the charge of antibody molecules, by ion-exchange chromatography. However, the above described analyses using chromatography techniques cannot distinguish minute structural changes of antibody molecules, such as changes in the sugar chain structures, and thus, the results obtained by such analyses are limited.

On the other hand, it has been reported that the performance of an antibody can be measured and determined by an analysis based on the affinity of the antibody to an affinity ligand immobilized on an insoluble carrier (Patent Document 3). However, the separation of an antibody based on the difference in the sugar chain structure, particularly, the separation of a human-derived antibody based on the difference in the sugar chain structure, has not been performed.

RELATED ART DOCUMENTS

Patent Documents

Patent Document 1: JP 2016-194500 A
Patent Document 2: JP 2016-099304 A
Patent Document 3: WO 2013/120929

Non-Patent Documents

Non-patent Document 1: CHROMATOGRAPHY, 34 (2), 83-88 (2013)
Non-patent Document 2: Science, 320, 373 (2008) Non-patent Document 3: Nature Communication, 7, 11205 (2016)

SUMMARY OF THE INVENTION

Problems to be Solved by the Invention

An object of the present invention is to provide a method for separating an antibody. In one embodiment, an object of the present invention is to provide a method for detecting the presence or absence of a disease, the risk of developing a disease, the degree of progression of a disease and/or the degree of progression of aging, in a subject.

Means for Solving the Problems

The present inventors have found out, as a result of intensive studies to solve the above mentioned problems, that it is possible to separate an antibody based on the difference in the sugar chain structure, by using an Fc-binding protein; and to detect the presence or absence of a disease, the risk of developing a disease, the degree of progression of a disease and/or the degree of progression of aging, in a subject, using as an indicator(s), a characteristic (s) of a separation pattern obtained upon separating an antibody obtained from the subject, using an Fc-binding protein, thereby completing the present invention.

That is, the present invention can be exemplified as follows.

[1] A method for detecting the presence or absence of a disease(s), the risk of developing a disease(s), the degree of progression of a disease(s), and/or the degree of progression of aging,
wherein the method comprises the following step (c):
(c) detecting the presence or absence of a disease(s), the risk of developing a disease(s), the degree of progression of a disease(s), and/or the degree of progression of aging, in a subject, using data of a separation pattern of an antibody(ies) as an indicator,
wherein the data are a characteristic(s) of the separation pattern of the antibody(ies),
wherein the data are obtained by the following steps (a) and (b):
(a) adding a solution containing an antibody obtained from the subject to a column filled with an insoluble carrier on which an Fc-binding protein is immobilized, to allow the antibody(ies) to be adsorbed on the carrier; and
(b) eluting the antibody(ies) adsorbed on the carrier using an eluent, to obtain the data.
[2] The method mentioned above, wherein the method comprises the steps (a) and (b), before performing the step (c).

[3] The method mentioned above, wherein the method comprises the step of adding an equilibrating liquid to the column to equilibrate the column, before performing the step (a).

[4] The method mentioned above, wherein the obtaining the data comprises the step of obtaining the separation pattern of the antibody(ies), and the step of extracting the characteristic(s) from the separation pattern.

[5] The method mentioned above, wherein the characteristic(s) is the peak area and/or the peak height.

[6] The method mentioned above, wherein the characteristic(s) is the peak area % and/or the peak height %.

[7] The method mentioned above, wherein the characteristic(s) is a characteristic(s) of one or more peaks selected from a first peak, a second peak, and a third peak.

[8] The method mentioned above, wherein the characteristic(s) is a characteristic(s) of the first peak.

[9] The method mentioned above, wherein the step (c) comprises the step of comparing the data with data of a separation pattern(s) of an antibody(ies) obtained from a control subject(s).

[10] The method mentioned above, wherein the disease(s) is one or more diseases selected from cancer, autoimmune diseases, infectious diseases, allergies, inflammatory diseases, cachexia, and age-related diseases.

[11] The method mentioned above, wherein the disease(s) is one or more diseases selected from pancreatic cancer, gastric cancer, breast cancer, colorectal cancer, renal cancer, rheumatism, Sjogren's syndrome, and pancreatitis.

[12] The method mentioned above, wherein the Fc-binding protein is any one of the following polypeptides (1) to (4):
  (1) a polypeptide comprising the 17th to 192nd amino acid residues of the amino acid sequence of SEQ ID NO: 1, wherein, in the 17th to 192nd amino acid residues, at least the 176th valine is substituted with phenylalanine;
  (2) a polypeptide comprising the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, the 171st phenylalanine is substituted with serine, and the 176th valine is substituted with phenylalanine;
  (3) a polypeptide comprising the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, and the 171st phenylalanine is substituted with serine; and
  (4) a polypeptide comprising the amino acid sequence of any one of the polypeptides (1) to (3), wherein the amino acid sequence comprises 1 to 10 amino acid mutations at a position(s) other than the above described substitution(s).

[13] A composition comprising two or more types of antibodies, wherein the composition satisfies two or more of the following I to IX:
  I. the value obtained by dividing the content of an antibody(ies) having G1Fa by the content of an antibody(ies) having G0F is 0.4 or less, in weight ratio;
  II. the value obtained by dividing the content of an antibody(ies) having G2F by the content of the antibody(ies) having G0F is 0.2 or less, in weight ratio;
  III. the value obtained by dividing the content of an antibody(ies) having G2F+2SA by the content of the antibody(ies) having G0F is 0.03 or less, in weight ratio;
  IV. the value obtained by dividing the content of an antibody(ies) having G1Fb by the content of the antibody(ies) having G1Fa is 0.5 or more, in weight ratio;
  V. the value obtained by dividing the content of the antibody(ies) having G2F by the content of the antibody(ies) having G1Fb is 0.6 or less, in weight ratio;
  VI. the value obtained by dividing the content of an antibody(ies) having G2F+SA by the content of the antibody(ies) having G1Fb is 0.3 or less, in weight ratio;
  VII. the value obtained by dividing the content of the antibody(ies) having G2F+2SA by the content of the antibody(ies) having G1Fb is 0.12 or less, in weight ratio;
  VIII. the ratio of the content of an antibody(ies) having G2+SA to the total content of the antibodies is 0.2% or less, in weight ratio; and
  IX. the ratio of the content of an antibody(ies) having G2+2SA to the total content of the antibodies is 0.2% or less, in weight ratio.

[14] A composition comprising two or more types of antibodies, wherein the composition satisfies two or more of the following I to IX:
  I. the value obtained by dividing the content of an antibody(ies) having G1Fa by the content of an antibody(ies) having G0F is 1.8 or more, in weight ratio;
  II. the value obtained by dividing the content of an antibody(ies) having G2F by the content of the antibody(ies) having G0F is 0.6 or more, in weight ratio;
  III. the value obtained by dividing the content of an antibody(ies) having G2F+2SA by the content of the antibody(ies) having G0F is 0.06 or more, in weight ratio;
  IV. the value obtained by dividing the content of an antibody(ies) having G1Fb by the content of the antibody(ies) having G1Fa is 0.3 or less, in weight ratio;
  V. the value obtained by dividing the content of the antibody(ies) having G2F by the content of the antibody(ies) having G1Fb is 3.0 or more, in weight ratio;
  VI. the value obtained by dividing the content of an antibody(ies) having G2F+SA by the content of the antibody(ies) having G1Fb is 0.6 or more, in weight ratio;
  VII. the value obtained by dividing the content of the antibody(ies) having G2F+2SA by the content of the antibody(ies) having G1Fb is 0.3 or more, in weight ratio;
  VIII. the ratio of the content of an antibody(ies) having G2+SA to the total content of the antibodies is 2% or more, in weight ratio; and
  IX. the ratio of the content of an antibody(ies) having G2+2SA to the total content of the antibodies is 0.6% or more, in weight ratio.

BRIEF DESCRIPTION OF THE DRAWINGS

FIG. 1 is a diagram showing a separation pattern obtained by analyzing a monoclonal antibody, using a column filled with an Fc-binding protein-immobilized gel.

FIG. 2 is a diagram showing a separation pattern obtained by analyzing human-derived gamma globulin, using a column filled with an Fc-binding protein-immobilized gel.

FIG. 3 is a diagram showing sugar chain structures of the monoclonal antibody contained in fractions obtained by separating and fractionating the monoclonal antibody, using a column filled with an Fc-binding protein-immobilized gel.

FIG. 4 is a diagram showing sugar chain structures of antibodies contained in fractions obtained by separating and fractionating the human-derived gamma globulin, using a column filled with an Fc-binding protein-immobilized gel.

FIG. 5 is a diagram showing separation patterns obtained by analyzing human-derived gamma globulin obtained from individuals of different ages, using a column filled with an Fc-binding protein-immobilized gel.

FIG. 6 is a diagram showing a plot of the values of the first peak area % obtained by analyzing human-derived gamma globulin obtained from individuals of different ages, using a column filled with an Fc-binding protein-immobilized gel.

FIG. 7 is a diagram showing plots of the values of the first peak area % obtained by analyzing gamma globulin derived from cancer patients, using a column filled with an Fc-binding protein-immobilized gel.

FIG. 8 is a diagram showing plots of the values of the first peak area % obtained by analyzing gamma globulin derived from autoimmune disease patients, using a column filled with an Fc-binding protein-immobilized gel.

FIG. 9 is a diagram showing a plot of the values of corrected first peak area % obtained by analyzing gamma globulin derived from cancer patients, using a column filled with an Fc-binding protein-immobilized gel.

FIG. 10 is a diagram showing plots of the values of the corrected first peak area % and the third peak area obtained by analyzing gamma globulin derived from patients with pancreatic cancer and pancreatitis, using a column filled with an Fc-binding protein-immobilized gel, as well as ROC curves for pancreatic cancer and pancreatitis.

FIG. 11 is a diagram showing a plot of the values of the corrected first peak area % obtained by analyzing gamma globulin derived from smoking and non-smoking healthy individuals, using a column filled with an Fc-binding protein-immobilized gel.

FIG. 12 is a diagram showing plots of the values of the first peak height % and the first peak area % obtained by analyzing human-derived gamma globulin obtained from individuals of different ages, using an FcR9_F column or an FcR9_V column filled with an Fc-binding protein-immobilized gel.

MODE FOR CARRYING OUT THE INVENTION

The present invention will now be described in detail.
<1> Methods

The present invention provides a method for separating an antibody using an Fc-binding protein. The above described method is also referred to as "the separation method according to the present invention".

The separation method according to the present invention may specifically be a method for separating an antibody, the method including the following steps (a) and (b):
(a) adding a solution containing an antibody to a column filled with an insoluble carrier on which an Fc-binding protein is immobilized, to allow the antibody to be adsorbed on the carrier; and
(b) eluting the antibody adsorbed on the carrier using an eluent.

The steps (a) and (b) are also referred to as "adsorption step" and "elution step", respectively.

The separation method according to the present invention may provide a separated antibody. That is, one embodiment of the separation method according to the present invention may be a method for producing a separated antibody, by separating an antibody using an Fc-binding protein. That is, one embodiment of the elution step may be the step of eluting the antibody adsorbed on the carrier using an eluent, to obtain an eluted antibody. In other words, one embodiment of the elution step may include the step of eluting the antibody adsorbed on the carrier using an eluent, and the step of obtaining an eluted antibody. The above described method is also referred to as "the antibody production method according to the present invention".

The antibody production method according to the present invention may specifically be a method for producing a separated antibody, the method including the following steps (a) and (b):
(a) adding a solution containing an antibody to a column filled with an insoluble carrier on which an Fc-binding protein is immobilized, to allow the antibody to be adsorbed on the carrier; and
(b) eluting the antibody adsorbed on the carrier using an eluent, to obtain an eluted antibody.

The separation method according to the present invention may provide data of a separation pattern of an antibody. That is, one embodiment of the separation method according to the present invention may be a method for producing data of a separation pattern of an antibody, by separating the antibody using an Fc-binding protein. That is, one embodiment of the elution step may be the step of eluting the antibody adsorbed on the carrier using an eluent, to obtain data of a separation pattern of the antibody. In other words, one embodiment of the elution step may include the step of eluting the antibody adsorbed on the carrier using an eluent, and the step of obtaining data of a separation pattern of the antibody. The above described method is also referred to as "the data production method according to the present invention". The data of a separation pattern of the antibody is also referred to as "separation data". The expressions "measuring data", "obtaining data" and "producing data" may be used synonymously.

The data production method according to the present invention may specifically be a method for producing separation data including the following steps (a) and (b):
(a) adding a solution containing an antibody to a column filled with an insoluble carrier on which an Fc-binding protein is immobilized, to allow the antibody to be adsorbed on the carrier; and
(b) eluting the antibody adsorbed on the carrier using an eluent, to obtain the separation data.

Using the separation data as an indicator, it is possible to detect the presence or absence of a disease, the risk of developing a disease, the degree of progression of a disease and/or the degree of progression of aging, in a subject. That is, the separation data may be regarded as the data to be used as an indicator for detecting the presence or absence of a disease, the risk of developing a disease, the degree of progression of a disease and/or the degree of progression of aging, in a subject. Specifically, the separation data obtained by separating an antibody obtained from a subject, using an Fc-binding protein, can be used as an indicator to detect the presence or absence of a disease, the risk of developing a disease, the degree of progression of a disease and/or the degree of progression of aging, in the subject. That is, the present invention provides a method for detecting the presence or absence of a disease, the risk of developing a disease, the degree of progression of a disease and/or the degree of progression of aging, in a subject, using as an indicator, separation data obtained by separating an antibody obtained from the subject, using an Fc-binding protein. The above described method is also referred to as "the detection method according to the present invention". The presence or absence of a disease, the risk of developing a disease, the degree of progression of a disease and/or the degree of progression of aging may also be collectively referred to as "the risk". The expressions "detecting the risk", "evaluating the risk" and "determining the risk" may be used synonymously.

The detection method according to the present invention may specifically be a method for detecting the presence or absence of a disease, the risk of developing a disease, the degree of progression of a disease and/or the degree of progression of aging, the method including the following step (c):

(c) detecting the presence or absence of a disease, the risk of developing a disease, the degree of progression of a disease and/or the degree of progression of aging, in a subject, using separation data as an indicator, wherein the data are obtained by the following steps (a) and (b):

(a) adding a solution containing an antibody obtained from the subject to a column filled with an insoluble carrier on which an Fc-binding protein is immobilized, to allow the antibody to be adsorbed on the carrier; and (b) eluting the antibody adsorbed on the carrier using an eluent, to obtain the data.

The detection method according to the present invention may include the steps (a) and (b). That is, the detection method according to the present invention may more specifically be a method for detecting the presence or absence of a disease, the risk of developing a disease, the degree of progression of a disease and/or the degree of progression of aging, the method including the following steps (a) to (c):

(a) adding a solution containing an antibody obtained from a subject to a column filled with an insoluble carrier on which an Fc-binding protein is immobilized, to allow the antibody to be adsorbed on the carrier;

(b) eluting the antibody adsorbed on the carrier using an eluent, to obtain separation data; and (c) detecting the presence or absence of a disease, the risk of developing a disease, the degree of progression of a disease and/or the degree of progression of aging, in the subject, using the data as an indicator.

The step (c) is also referred to as "detection step".

These methods are also collectively referred to as "the method according to the present invention"

<Adsorption Step>

The adsorption step is the step of adding a solution containing an antibody to a column filled with an insoluble carrier on which an Fc-binding protein is immobilized, to allow the antibody to be adsorbed on the carrier.

The term "antibody" refers to a molecule containing the Fc region. The antibody may be one consisting of the Fc region, or one containing another region in addition to the Fc region. Examples of the Fc region include the Fc region of an immunoglobulin. A sugar chain may be added to the antibody. For example, a sugar chain may be added at least to the Fc region of the antibody. The antibody may be a monoclonal antibody or a polyclonal antibody. The source from which the antibody is derived is not particularly limited. The antibody may be derived from a single organism, or derived from a combination of two or more types of organisms. The antibody may be, for example, a chimeric antibody, a humanized antibody, a human antibody, or a variant thereof (such as an amino acid substitution product). Examples of the antibody include immunoglobulins. Examples of immunoglobulins include IgG, IgM, IgA, IgD and IgE. In particular, examples of immunoglobulins include IgG. Examples of IgG include IgG1, IgG2, IgG3 and IgG4. Further, the antibody may also be, for example, a bispecific antibody; a fusion antibody of the Fc region and another protein; or an antibody with an artificially modified structure, such as a composite (ADC) of the Fc region and a drug. The antibody may be, for example, an antibody drug. Examples of the antibody drug include: infliximab which is an anti-TNF-α antibody; tocilizumab which is an anti-IL-6 antibody; and trastuzumab which is an antibody against a cancer gene, HER2. The antibody can be produced, for example, by antibody producing cells, such as CHO cells, Sp2/0 cells, NS0 cells and hybridoma cells.

Examples of the sugar chain include sugar chain structures shown in FIG. 3 and FIG. 4. In particular, examples of a sugar chain capable of contributing to the separation of an antibody include G0, G0F, G1, G0F+GN, G1Fa, G1Fb, G1F+GN, G2, G2F, G1F+SA, G2F+SA, G2F+2SA, G2F+GN, G2+SA, G2+2SA, S1, S2 and S3.

Human-derived antibodies usually contain an antibody having sialic acid. The content of the antibody(ies) having sialic acid in the human-derived antibodies can be, for example, from about 0.1 to 20%, in weight ratio, with respect to the total content of the antibodies. In many cases, two sialic acid molecules are attached to the sugar chain terminal of a human-derived antibody. Further, human-derived antibodies can contain a bisecting GlcNAc (indicated as "+GN" in Table 5) in a weight ratio of from about 1 to 20%, with respect to the total content of the antibodies. On the other hand, a bisecting GlcNAc is not usually present in hamster- and mouse-derived antibodies, and the number of sialic acid molecules attached to the sugar chain terminal is from 0 to 1.

The antibody to be subjected to the adsorption step may be a mixture containing a plurality of kinds of antibody molecules. Specifically, the antibody to be subjected to the adsorption step may be a mixture containing a plurality of kinds of antibody molecules having different sugar chain structures. More specifically, the antibody to be subjected to the adsorption step may be a mixture containing a plurality of kinds of antibody molecules having Fc regions to which different sugar chain structures are added.

When performed for the purpose of detecting the risk, the method according to the present invention may be carried out using an antibody obtained from a subject.

The term "subject" refers to a human individual whose risk is to be detected. The subject as used herein is also referred to as a "target subject" in order to distinguish from a control subject to be described later. The subject is not particularly limited, as long as an antibody sample derived therefrom can be used, namely, as long as an antibody sample can be obtained, or has already been obtained, from the subject. The subject may be a male or a female. The subject may be an individual of any generation, such as a child, a youth, a middle-aged person or an elderly person. The subject may or may not be a healthy individual.

The term "antibody sample" refers to a sample containing an antibody. Examples of the antibody sample include: blood samples such as blood (whole blood), diluted blood, serum, plasma, spinal fluid, umbilical cord blood and component blood samples; samples which can contain blood-derived components such as urine, saliva, semen, feces, phlegm, amniotic fluid and ascites; tissue fragments or cells of liver, lung, spleen, kidney, skin, tumors and lymph nodes; and an antibody separated therefrom. The antibody sample may be used in the adsorption step, as it is, or after being subjected to a pre-treatment as appropriate. The pre-treatment may be carried out, for example, by an ordinary method. Examples of the pre-treatment include purification by centrifugation or using a column. Specifically, for example, gamma globulin may be purified to be used in the adsorption step. The antibody sample can be used in the adsorption step, in the form of a solution containing an antibody. That is, the antibody sample may be prepared in the form of a solution containing an antibody, as appropriate, to be used in the adsorption step. For example, the antibody sample as exemplified above or a pre-treated product thereof may be dissolved, suspended or dispersed in a liquid medium, or subjected to a solvent exchange or the like, as appropriate, to be used as a solution containing an antibody in the adsorption step. For example, the description of an equilibrating liquid to be described later can be applied correspondingly to the liquid medium described above. The liquid medium may be the same as, or different from, the equilibrating liquid.

The description of an antibody obtained from a subject can also be applied correspondingly to the use of another antibody. For example, an arbitrary antibody other than the antibody obtained from a subject, may likewise be used in the adsorption step in the form of a solution containing an antibody, as it is, or after being subjected to a pre-treatment, as appropriate.

The term "Fc-binding protein" refers to a protein capable of binding to the Fc region of an antibody. The Fc-binding protein is not particularly limited, as long as it allows for obtaining a desired separation pattern of an antibody. An antibody can be separated, for example, based on the difference in affinity to the Fc-binding protein, which is based on the difference in the sugar chain structure (for example, the structure of a sugar chain bound to the Fc region) of the antibody. The affinity of an antibody (specifically, the affinity of the sugar chain structure of the antibody) to the Fc-binding protein can correlate, for example, to the functions of the antibody, such as drug efficacy. Further, the affinity of an antibody (specifically, the affinity of the sugar chain structure of the antibody) to the Fc-binding protein can correlate, for example, to the risk in a subject. That is, the Fc-binding protein is preferably a protein which is, for example, capable of binding to the Fc region of an antibody, and capable of recognizing the difference in the sugar chain structure (for example, the structure of a sugar chain bound to the Fc region) of the antibody. The Fc-binding protein may be, for example, a human Fc-binding protein. Examples of the human Fc-binding protein include Fc-binding proteins found in humans, and variants thereof. Specific examples of the human Fc-binding protein include a protein containing the full-length sequence or a partial sequence of the amino acid sequence of the extracellular region of human FcγRIIIa. Examples of the amino acid sequence of the extracellular region of human FcγRIIIa include, in the case of a naturally-occurring human FcγRIIIa, the region from the 17th glycine to the 192nd glutamine of the amino acid sequence of SEQ ID NO: 1. Examples of the partial sequence of the amino acid sequence of the extracellular region of human FcγRIIIa include the amino acid sequence of a region capable of exhibiting the function of binding at least to the Fc region (such as the Fc region of human IgG), of the extracellular region of human FcγRIIIa. One example of the human Fc-binding protein may be a polypeptide of the following (i) or (ii):

(i) a polypeptide which contains at least the 17th to 192nd amino acid residues of the amino acid sequence of SEQ ID NO: 1; or (ii) a polypeptide which contains at least the 17th to 192nd amino acid residues of the amino acid sequence of SEQ ID NO: 1, and in which the amino acid residues contain one or more amino acid substitutions, insertions and/or deletions.

Examples of one embodiment of the above described (ii) include a polypeptide which contains the 17th to 192nd amino acid residues of the amino acid sequence of SEQ ID NO: 1, and in which the 17th to 192nd amino acid residues contain at least any one of the following amino acid substitutions (1) to (40) (JP 2015-086216 A):

(1) the 18th methionine of SEQ ID NO: 1 is substituted with arginine;

(2) the 27th valine of SEQ ID NO: 1 is substituted with glutamic acid;

(3) the 29th phenylalanine of SEQ ID NO: 1 is substituted with leucine or serine;

(4) the 30th leucine of SEQ ID NO: 1 is substituted with glutamine;

(5) the 35th tyrosine of SEQ ID NO: 1 is substituted with aspartic acid, glycine, lysine, leucine, asparagine, proline, serine, threonine, or histidine;

(6) the 46th lysine of SEQ ID NO: 1 is substituted with isoleucine or threonine;

(7) the 48th glutamine of SEQ ID NO: 1 is substituted with histidine or leucine;

(8) the 50th alanine of SEQ ID NO: 1 is substituted with histidine;

(9) the 51st tyrosine of SEQ ID NO: 1 is substituted with aspartic acid or histidine;

(10) the 54th glutamic acid of SEQ ID NO: 1 is substituted with aspartic acid or glycine;

(11) the 56th asparagine of SEQ ID NO: 1 is substituted with threonine;

(12) the 59th glutamine of SEQ ID NO: 1 is substituted with arginine;

(13) the 61st phenylalanine of SEQ ID NO: 1 is substituted with tyrosine;

(14) the 64th glutamic acid of SEQ ID NO: 1 is substituted with aspartic acid;

(15) the 65th serine of SEQ ID NO: 1 is substituted with arginine;

(16) the 71st alanine of SEQ ID NO: 1 is substituted with aspartic acid;

(17) the 75th phenylalanine of SEQ ID NO: 1 is substituted with leucine, serine or tyrosine;

(18) the 77th aspartic acid of SEQ ID NO: 1 is substituted with asparagine;

(19) the 78th alanine of SEQ ID NO: 1 is substituted with serine;

(20) the 82nd aspartic acid of SEQ ID NO: 1 is substituted with glutamic acid or valine;

(21) the 90th glutamine of SEQ ID NO: 1 is substituted with arginine;

(22) the 92nd asparagine of SEQ ID NO: 1 is substituted with serine;

(23) the 93rd leucine of SEQ ID NO: 1 is substituted with arginine or methionine;

(24) the 95th threonine of SEQ ID NO: 1 is substituted with alanine or serine;

(25) the 110th leucine of SEQ ID NO: 1 is substituted with glutamine;
(26) the 115th arginine of SEQ ID NO: 1 is substituted with glutamine;
(27) the 116th tryptophan of SEQ ID NO: 1 is substituted with leucine;
(28) the 118th phenylalanine of SEQ ID NO: 1 is substituted with tyrosine;
(29) the 119th lysine of SEQ ID NO: 1 is substituted with glutamic acid;
(30) the 120th glutamic acid of SEQ ID NO: 1 is substituted with valine;
(31) the 121st glutamic acid of SEQ ID NO: 1 is substituted with aspartic acid or glycine;
(32) the 151st phenylalanine of SEQ ID NO: 1 is substituted with serine or tyrosine;
(33) the 155th serine of SEQ ID NO: 1 is substituted with threonine;
(34) the 163rd threonine of SEQ ID NO: 1 is substituted with serine;
(35) the 167th serine of SEQ ID NO: 1 is substituted with glycine;
(36) the 169th serine of SEQ ID NO: 1 is substituted with glycine;
(37) the 171st phenylalanine of SEQ ID NO: 1 is substituted with tyrosine;
(38) the 180th asparagine of SEQ ID NO: 1 is substituted with lysine, serine or isoleucine;
(39) the 185th threonine of SEQ ID NO: 1 is substituted with serine; and
(40) the 192nd glutamine of SEQ ID NO: 1 is substituted with lysine.

Further, examples of another embodiment of the above described (ii) include a polypeptide which contains the 17th to 192nd amino acid residues of the amino acid sequence of SEQ ID NO: 1, and in which the 17th to 192nd amino acid residues contain at least any one of the following amino acid substitutions (41) to (57) (JP 2016-169197 A):
(41) the 29th phenylalanine of SEQ ID NO: 1 is substituted with isoleucine or leucine;
(42) the 39th glutamic acid of SEQ ID NO: 1 is substituted with glycine;
(43) the 48th glutamine of SEQ ID NO: 1 is substituted with arginine
(44) the 51st tyrosine of SEQ ID NO: 1 is substituted with serine;
(45) the 61st phenylalanine of SEQ ID NO: 1 is substituted with tyrosine;
(46) the 77th aspartic acid of SEQ ID NO: 1 is substituted with glycine;
(47) the 82nd aspartic acid of SEQ ID NO: 1 is substituted with glutamic acid;
(48) the 90th glutamine of SEQ ID NO: 1 is substituted with arginine
(49) the 112nd glutamine of SEQ ID NO: 1 is substituted with leucine;
(50) the 117th valine of SEQ ID NO: 1 is substituted with glutamic acid;
(51) the 119th lysine of SEQ ID NO: 1 is substituted with asparagine or glutamic acid;
(52) the 140th threonine of SEQ ID NO: 1 is substituted with isoleucine;
(53) the 142nd leucine of SEQ ID NO: 1 is substituted with glutamine;
(54) the 171st phenylalanine of SEQ ID NO: 1 is substituted with serine
(55) the 175th leucine of SEQ ID NO: 1 is substituted with arginine;
(56) the 180th asparagine of SEQ ID NO: 1 is substituted with serine; and
(57) the 188th isoleucine of SEQ ID NO: 1 is substituted with valine.

Further, examples of still another embodiment of the above described (ii) include a polypeptide which contains the 17th to 192nd amino acid residues of the amino acid sequence of SEQ ID NO: 1, and in which the 17th to 192nd amino acid residues contain at least any one of the following amino acid substitutions (58) to (61) (JP 2016-169197 A):
(58) the 66th leucine of SEQ ID NO: 1 is substituted with histidine or arginine;
(59) the 147th glycine of SEQ ID NO: 1 is substituted with aspartic acid;
(60) the 158th tyrosine of SEQ ID NO: 1 is substituted with histidine; and
(61) the 176th valine of SEQ ID NO: 1 is substituted with phenylalanine.

Further, examples of yet still another embodiment of the above described (ii) include a polypeptide which contains the 17th to 192nd amino acid residues of the amino acid sequence of SEQ ID NO: 1, and in which the 17th to 192nd amino acid residues contain at least any one of the above described amino acid substitutions (1) to (61).

In particular, examples of the above described (ii) include the following polypeptides (ii-1) to (ii-3):
(ii-1) a polypeptide containing the 17th to 192nd amino acid residues of the amino acid sequence of SEQ ID NO: 1, wherein, in the 17th to 192nd amino acid residues, at least the 176th valine is substituted with phenylalanine;
(ii-2) a polypeptide containing the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, the 171st phenylalanine is substituted with serine, and the 176th valine is substituted with phenylalanine; and
(ii-3) a polypeptide containing the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, and the 171st phenylalanine is substituted with serine.

The Fc-binding protein may be a polypeptide which contains "one to several" amino acid mutations (for example, substitutions, insertions and/or deletions) in the amino acid sequence of any one of the Fc-binding proteins exemplified above (such as the polypeptide of the above described (i) or (ii)), as long as the polypeptide has a function of binding to the Fc region (such as the Fc region of human IgG). The expression "one to several" as used herein may refer to, for example, from 1 to 50, preferably from 1 to 40, more preferably from 1 to 30, still more preferably 1 to 20, and particularly preferably from 1 to 10. The "one to several" amino acid mutations may occur, for example, such that the amino acid substitution(s) selected from the above described amino acid substitutions (1) to (61) and included in any one of the Fc-binding proteins exemplified above, is/are conserved. In other words, the "one to several" amino acid mutations may occur, for example, at a position(s) other than the position(s) of the amino acid substitution(s) selected from the above described amino acid substitutions (1) to (61) and included in any one of the Fc-binding proteins exemplified above.

The Fc-binding protein may be a polypeptide containing the amino acid sequence having a high homology to the amino acid sequence of any one of the Fc-binding proteins exemplified above (such as the polypeptide of the above described (i) or (ii)), as long as the polypeptide has a function of binding to the Fc region (such as the Fc region of human IgG). The expression "high homology" may refer to a homology of 70% or more, 80% or more, 90% or more, or 95% or more. The term "homology" may refer to "similarity" or "identity". The "homology" may particularly refer to "identity". The homology between amino acid sequences can be determined using an alignment program, such as BLAST. For example, the "identity between amino acid sequences" may refer to the identity between amino acid sequences calculated using blastp, specifically, to the identity between amino acid sequences calculated using blastp with default parameters. Changes in the amino acid sequence within the homology range as described above may occur, for example, such that the amino acid substitution(s) selected from the above described amino acid substitutions (1) to (61) and included in any one of the Fc-binding proteins exemplified above, is/are conserved. In other words, changes in the amino acid sequence within the homology range as described above may occur, for example, at a position(s) other than the position(s) of the amino acid substitution(s) selected from the above described amino acid substitutions (1) to (61) and included in any one of the Fc-binding proteins exemplified above.

The Fc-binding protein can be produced for example, by allowing a host which contains a gene encoding the Fc-binding protein to express the gene. The gene encoding the Fc-binding protein can be obtained, for example, by cloning, chemical synthesis, introduction of a mutation(s), or combination thereof. The host is not particularly limited, as long as it is capable of expressing the Fc-binding protein. Examples of the host include animal cells, insect cells and microorganisms. Examples of animal cells include COS cells, CHO cells, Hela cells, NIH 3T3 cells and HEK 293 cells. Examples of insect cells include Sf9 and BTI-TN-5B1-4. Examples of microorganisms include yeasts and bacteria. Examples of yeasts include: yeasts belonging to the genus *Saccharomyces*, such as *Saccharomyces cerevisiae*; yeasts belonging to the genus *Pichia*, such as *Pichia Pastoris*; and yeasts belonging to the genus *Schizosaccharomyces*, such as *Schizosaccharomyces pombe*. Examples of bacteria include bacteria belonging to the genus *Escherichia*, such as *Escherichia coli*. Examples of *Escherichia coli* include W3110 strain, JM109 strain and BL21 (DE3) strain. Further, the Fc-binding protein can also be produced, for example, by expressing a gene encoding the Fc-binding protein in a cell-free protein synthesis system.

The term "insoluble carrier" refers to a carrier insoluble in a liquid (for example, a liquid used for the adsorption or elution of an antibody, such as an equilibrating liquid or an eluent) to be passed through a column, in the method according to the present invention. The insoluble carrier may contain a functional group (such as hydroxy group) for immobilizing the Fc-binding protein via a covalent bond. Examples of the insoluble carrier include: carriers derived from inorganic substances such as zirconia, zeolite, silica and coated silica; carriers derived from naturally-occurring organic polymeric substances such as cellulose, agarose and dextran; and carriers derived from synthetic organic polymeric substances such as polyacrylic acid, polystyrene, polyacrylamide, polymethacrylamide, polymethacrylate and vinyl polymers.

The Fc-binding protein can be immobilized on the insoluble carrier, as appropriate. The Fc-binding protein can be immobilized on the insoluble carrier via a covalent bond, for example, using a functional group (such as hydroxy group) which is contained in the insoluble carrier and which is for immobilizing the Fc-binding protein via a covalent bond. In cases where the insoluble carrier contains a hydroxy group on its surface, for example, an activator can be used to form an activating group capable of covalently binding to the Fc-binding protein, from the hydroxy group, thereby covalently binding the activating group and the Fc-binding protein. Specific examples of the activator for hydroxy group include epichlorohydrin (forms an epoxy group as the activating group), 1,4-butanediol diglycidyl ether (forms an epoxy group as the activating group), tresyl chloride (forms a tresyl group as the activating group), and vinyl bromide (forms a vinyl group as the activating group). It is also possible to convert a hydroxy group into an amino group, a carboxyl group or the like, followed by activation by the activator. Specific examples of the activator for amino group, carboxyl group or the like include N-succinimidyl 3-maleimidopropionate (forms a maleimide group as the activating group), 1,1'-carbonyldiimidazole (forms a carbonylimidazole group as the activating group), and halogenated acetic acid (forms a halogenated acetyl group as the activating group).

By adding a solution containing an antibody to a column filled with the insoluble carrier on which the Fc-binding protein is immobilized, the antibody can be adsorbed on the carrier. The solution containing an antibody can be added to the column, for example, using a liquid feeding means such as a pump. The operation of adding a liquid to a column is also expressed as "feeding a liquid to a column". The conditions for carrying out the adsorption step, such as the amount to be added of the solution containing an antibody, the type of liquid phase, the feeding rate of the liquid phase and the column temperature, are not particularly limited, as long as the antibody can be adsorbed on the carrier. The conditions for carrying out the adsorption step can be set as appropriate, depending on various conditions, such as the type of the antibody, the type of the Fc-binding protein, the type of the insoluble carrier and the scale of the column. Examples of the liquid phase include the equilibrating liquid to be described later. The liquid feeding rate may be, for example, from 0.1 mL/min to 1.5 mL/min, from 0.2 mL/min to 1.0 mL/min or from 0.4 mL/min to 0.8 mL/min, when the column has an inner diameter of 4.6 mm. The liquid feeding rate may be set, for example, so as to be proportional to the square of the inner diameter of the column. The column temperature may be, for example, from 0 to 50° C.

Before adding the solution containing an antibody to the column, an equilibrating liquid may be used to equilibrate the column. That is, the method according to the present invention may include the step of adding an equilibrating liquid to the column to equilibrate the column, before performing the adsorption step. The equilibrating liquid may be, for example, an aqueous buffer solution. Specifically, the equilibrating liquid may be, for example, a weak acidic buffer solution having a pH of from 4.0 to 6.9. The components of the buffer solution can be selected as appropriate, depending on various conditions, such as the pH of the buffer solution. Examples of the components of the buffer solution include phosphoric acid, acetic acid, formic acid, MES (2-morpholinoethanesulfonic acid), MOPS (3-morpholinopropanesulfonic acid), citric acid, succinic acid, glycine and piperazine.

<Elution Step>

The elution step is the step of eluting the antibody adsorbed on the carrier using an eluent.

In other words, the antibody adsorbed on the carrier can be eluted by adding an eluent to the column. The conditions for carrying out the elution step, such as the type of the eluent, the feeding mode of the eluent, the feeding rate of the liquid phase and the column temperature, are not particularly limited, as long as the antibody can be separated in a desired form, for example, as long as a desired separation data can be obtained. The conditions for carrying out the elution step can be set as appropriate, depending on various conditions, such as the type of the antibody, the type of the Fc-binding protein, the type of the insoluble carrier and the scale of the column. As the eluent, one that weakens the affinity of the antibody to the Fc-binding protein can be used. The eluent may be, for example, an aqueous buffer solution having a pH lower than that of the liquid phase (such as an equilibrating liquid) before the elution. Specifically, the eluent may be, for example, an acidic buffer solution having a pH of from 2.5 to 4.5. In cases where the liquid phase (such as an equilibrating liquid) before the elution is a weak acidic buffer solution having a pH of from 4.0 to 6.9, for example, the eluent may be an acidic buffer solution having a pH of from 2.5 to 4.5. The components of the buffer solution can be selected as appropriate, depending on various conditions, such as the pH of the buffer solution. Examples of the components of the buffer solution include phosphoric acid, acetic acid, formic acid, MES (2-morpholinoethanesulfonic acid), MOPS (3-morpholinopropanesulfonic acid), citric acid, succinic acid, glycine and piperazine. The feeding mode of the eluent may be, for example, a gradient mode or an isocratic mode. In particular, the feeding mode of the eluent may be a gradient mode. That is, the elution may particularly be carried out by gradually increasing the ratio of the eluent in the liquid phase. The gradient mode may be, for example, a linear gradient mode, a stepwise gradient mode, or a combination thereof. Specifically, the gradient mode may be set, for example, such that the ratio of the eluent in the liquid phase is increased from 0% (v/v) to 100% (v/v) within the period of time from 10 to 60 minutes, from 15 to 50 minutes or from 20 to 40 minutes. The liquid feeding rate may be, for example, from 0.1 mL/min to 1.5 mL/min, from 0.2 mL/min to 1.0 mL/min or from 0.4 mL/min to 0.8 mL/min, when the column has an inner diameter of 4.6 mm. The liquid feeding rate may be set, for example, so as to be proportional to the square of the inner diameter of the column. The column temperature may be, for example, from 0 to 50° C.

The elution step may provide a separated antibody. The separated antibody may be obtained, for example, as an eluted fraction containing the antibody. That is, the separated antibody can be obtained by fractionating the eluted fraction containing the separated antibody. The eluted fraction can be fractionated, for example, by an ordinary method. Specifically, the eluted fraction can be fractionated, for example, by an automatic fraction collector, such as an autosampler. Further, the separated antibody can be collected from the eluted fraction. The separated antibody can be collected from the eluted fraction, for example, by an ordinary method. Specifically, the separated antibody can be collected from the eluted fraction, for example, by a known method used for the separation and purification of a protein.

The elution step may provide separation data (namely, data of a separation pattern of the antibody). The separation data are not particularly limited, as long as the data can be used as an indicator for detecting the risk in a subject, namely, as long as the data correlate with the risk in a subject. The separation data may be, for example, a characteristic of the separation pattern of the antibody. The characteristic of the separation pattern of the antibody is also simply referred to as the "characteristic". That is, the step of obtaining the separation data may include, for example, the step of obtaining the separation pattern of the antibody, and the step of extracting the characteristic of the separation pattern of the antibody (namely, extracting the characteristic of the pattern from the separation pattern of the antibody). The separation pattern of the antibody can be obtained by detecting the antibody with a detector. Examples of the detector include UV detectors and mass detectors. Examples of the separation pattern of the antibody include a chromatogram obtained upon elution of the antibody. Examples of the characteristic include a parameter which can be obtained from the separation pattern of the antibody and which correlates with the risk in a subject. Specific examples of the characteristic include a characteristic of an elution peak (namely, a peak of the eluted antibody). Specific examples of the characteristic of an elution peak include: the peak area, the peak elution time, the peak width, the number of peaks detected and the peak height, of the elution peak The elution peak whose characteristic(s), such as the peak area and/or the peak height, is/are to be extracted is also referred to as a "target peak" In particular, examples of the characteristic of the elution peak include the peak area and the peak height. The separation pattern of the antibody can be used for the extraction of the characteristic, as it is, or after being subjected to a correction, such as the correction of the base line, as appropriate. The characteristic may be an absolute value or a relative value. Examples of the relative value include the ratio or difference with respect to the value of another elution peak (namely, any one of the elution peaks other than the target peak), and the ratio or difference with respect to the total value of all the elution peaks (namely, all the elution peaks including the target peak). In particular, examples of the relative value include the ratio with respect to the value of another elution peak, and the ratio with respect to the total value of all the elution peaks. As the other elution peak, one elution peak can be used alone, or two or more elution peaks can be used in combination. The peak area may specifically be, for example, the peak area %. The term "peak area %" refers to the ratio (%) of the area of the target peak with respect to the total value of the areas of all the elution peaks. Further, the peak height may specifically be, for example, the peak height %. The term "peak height %" refers to the ratio (%) of the height of the target peak with respect to the total value of the heights of all the elution peaks. The characteristic may be subjected to a correction, such as a correction based on the peak of an internal standard substance, or a correction based on a feature of a subject. For example, the characteristic may be corrected based on the age of a subject. That is, for example, when the characteristic is affected by the age of a subject, the extracted characteristic may be corrected based on the age of the subject, before being used in the detection step. The characteristic corrected based on the age of the subject can be used, for example, for detecting the risk of symptoms other than aging.

The target peak can be selected as appropriate, depending on various conditions, such as the type of the risk and the like. Examples of the target peak include the first to fourth peaks. In particular, examples of the target peak include the first peak, the second peak and the third peak. Further in particular, examples of the target peak include the first peak. The first peak can be suitably used, for example, for evaluating the risk of symptoms other than pancreatitis. The second peak can be suitably used, for example, for evaluating the risk of aging. The third peak can be suitably used, for example, for evaluating the risk of pancreatitis. Specifically, the third peak can be used, for example, for distinguishing between pancreatitis and pancreatic cancer. As the target peak, one elution peak may be used, or two or more elution peaks may be used in combination. The expression "the first to fourth peaks" may refer to peaks eluted first to fourth after the start of the elution (for example, after the start of the gradient), respectively, unless otherwise stated. In particular, the target peak may be a peak having a peak area % of 1% or more. In other words, "the first to fourth peaks" may particularly refer to peaks which are eluted first to fourth after the start of the elution, respectively, and each of which has a peak area % of 1% or more. Further, in cases where the elution step is carried out by a gradient elution, the "first peak" may refer, for example, to the peak eluted first after the pH of the liquid phase reaches 5.4 or less, 5.2 or less, 5.0 or less, or 4.8 or less. Still further, in cases where the elution step is carried out by a gradient elution, the "first peak" may refer, for example, to the peak eluted during the period in which the pH of the liquid phase is within the range of from 5.4 to 4.4, from 5.2 to 4.5 or from 5.0 to 4.6. The pH of the liquid phase is calculated in accordance with the following equation (I), when the pH of the liquid phase (such as an equilibrating liquid) before the start of the elution is defined as X, the pH of the eluent is defined as Y, and the ratio of the eluent in the liquid phase is defined as Z %. It is noted that the pH at which the peak was eluted is corrected as appropriate, taking into consideration the capacity of the flow path, such as the capacity of the column used.

$$\text{pH of liquid phase} = X - ((X-Y) \times Z/100) \quad (I)$$

<Detection Step>

The detection step is the step of detecting the risk (namely, the presence or absence of a disease, the risk of developing a disease, the degree of progression of a disease and/or the degree of progression of aging) in a subject, using the separation data (namely, the data of the separation pattern of the antibody) as an indicator.

Examples of the disease include diseases affected by the activity (such as injurious effect or phagocytosis) of immune cells. Examples of immune cells include natural killer cells, monocytes and macrophages Specific examples of the disease include cancer, autoimmune diseases, infectious diseases, allergies and inflammatory diseases. All of these diseases can be diseases affected by the activity of immune cells.

Examples of cancer include brain tumor, breast cancer, endometrial cancer, cervical cancer, ovarian cancer, esophageal cancer, gastric cancer, appendix cancer, colorectal cancer, hepatic cancer, gallbladder cancer, bile duct cancer, pancreatic cancer, adrenal cancer, gastrointestinal stromal tumor (GIST), mesothelioma, head and neck cancer, renal cancer, lung cancer, osteosarcoma, Ewing sarcoma, chondrosarcoma, prostate cancer, testicular tumor, renal cell carcinoma, bladder cancer, rhabdomyosarcoma, skin cancer and anal cancer. In particular, examples of cancer include pancreatic cancer, gastric cancer, breast cancer, colorectal cancer and renal cancer.

Examples of autoimmune diseases include Guillain-Barre syndrome, myasthenia gravis, multiple sclerosis, chronic gastritis, chronic atrophic gastritis, autoimmune hepatitis, primary biliary cholangitis, ulcerative colitis, Crohn's disease, primary biliary cholangitis, autoimmune pancreatitis, Takayasu arteritis, Goodpasture's syndrome, rapidly progressive glomerulonephritis, megaloblastic anemia, autoimmune hemolytic anemia, autoimmune neutropenia, idiopathic thrombocytopenic purpura, Graves' disease, Hashimoto's disease, primary hypothyroidism, idiopathic Addison's disease, type 1 diabetes, chronic discoid lupus erythematosus, localized scleroderma, pemphigus, pustular psoriasis, psoriasis vulgaris, pemphigoid, herpes gestationis, linear IgA bullous dermatosis, acquired epidermolysis bullosa, alopecia areata, vitiligo vulgaris, Sutton's acquired leukoderma/Sutton's nevus, Harada disease, autoimmune optic neuropathy, autoimmune inner ear disorder, idiopathic azoospermia, habitual abortion, rheumatism, systemic lupus erythematosus, antiphospholipid antibody syndrome, polymyositis, dermatomyositis, scleroderma, Sjogren's syndrome, IgG4 related diseases, vasculitis syndrome and mixed connective tissue disease. In particular, examples of the autoimmune disease include rheumatism and Sjogren's syndrome.

Examples of infectious diseases include bacterial infections, fungal infections, parasitic protozoal infections, parasitic helminth infections and viral infections. Examples of bacterial infections include: infections caused by various types of bacteria, such as *Streptococcus, Staphylococcus aureus, Staphylococcus epidermidis, Enterococcus, Listeria, Neisseria meningitidis, Neisseria gonorrhoeae, Pathogenic E. coli, Klebsiella, Proteus, Bordetella pertussis, Pseudomonas aeruginosa, Serratia, Citrobacter, Acinetobacter, Enterobacter, Mycoplasma, Clostridium*, rickettsia and *chlamydia*; tuberculosis; nontuberculous mycobacteriosis; cholera, plague; diphtheria; dysentery; scarlet fever; anthrax; syphilis; tetanus; leprosyv legionella pneumonia; leptospirosis; Lyme disease; tularemia; and Q fever. Examples of fungal infections include aspergillosis, candidiasis, cryptococcosis, trichophytosis, histoplasmosis and *Pneumocystis* pneumonia (*Carini*) pneumonia). Examples of parasitic protozoal infections include amebic dysentery, malaria, toxoplasmosis, leishmaniasis and cryptosporidiosis. Examples of parasitic helminth infections include echinococcosis, *Schistosoma japonicum* infection, filariasis, ascariasis and diphyllobothriasis. Examples of viral infections include, influenza, viral hepatitis, viral meningitis, viral gastroenteritis, viral conjunctivitis, acquired immunodeficiency syndrome (AIDS), adult T-cell leukemia, Ebola hemorrhagic fever, yellow fever, cold syndrome, rabies, cytomegalovirus infection, severe acute respiratory syndrome (SARS), Middle East respiratory syndrome (MERS), progressive multifocal leukoencephalopathy, chickenpox/herpes zoster, herpes simplex, hand-foot-and-mouth disease, dengue fever, Japanese encephalitis, infectious erythema, infectious mononucleosis, smallpox, rubella, acute poliomyelitis (polio), measles, pharyngoconjunctival fever (pool fever), Marburg hemorrhagic fever, renal symptomatic hemorrhagic fever, Lassa fever, mumps, West Nile fever, herpangina and Chikungunya fever. The infectious diseases may be, for example, opportunistic infectious diseases.

Examples of allergies include, anaphylactic shock, allergic rhinitis, conjunctivitis, bronchial asthma, urticaria, atopic dermatitis, hemolytic anemia, idiopathic thrombocytopenic purpura, drug-induced hemolytic anemia, granulocytopenia, thrombocytopenia, Goodpasture syndrome, Serum disease, systemic lupus erythematosus (SLE), rheumatism, glomerulonephritis, hypersensitivity pneumonia, allergic bronchopulmonary aspergillosis (ABPA), contact dermatitis, allergic encephalitis, transplant rejection, tuberculous cavity and epithelioid granuloma.

Examples of inflammatory diseases include diseases induced by proinflammatory cytokines. Examples of proinflammatory cytokines include IL-6 and TNF-α. Specific examples of inflammatory diseases include encephalomyelitis, osteomyelitis, meningitis, neuritis, ocular inflammations (such as dacryoadenitis, scleritis, episcleritis, keratitis, chorioretinitis, retinitis, chorioretinitis, blepharitis, conjunctivitis, uveitis, etc.), ear inflammations (such as external otitis, otitis media and otitis interna), mastitis, carditis (such as endocarditis, myocarditis and pericarditis), vasculitis (such as arteritis, phlebitis and capillary vasculitis), respiratory inflammations (such as sinusitis, rhinitis, pharynx gitis, laryngitis, tracheitis, bronchitis, bronchiolitis, pneumonia, pleurisy and mediastinitis), oral inflammations (such as stomatitis, gingivitis, gingival stomatitis, glossitis, tonsillitis, sialadenitis, parotitis, cheilitis, pulpitis and rhinitis), gastrointestinal inflammations (such as esophagitis, gastritis, gastroenteritis, enteritis, small intestine enteritis, colitis, duodenitis, ileitis, appendicitis and proctitis), dermatitis, cellulitis, hidradenitis, arthritis, dermatomyositis, myositis, synovitis, tendinitis, panniculitis, osteitis, osteomyelitis, periostitis, nephritis, ureteritis, cystitis, ureteritis, ovitis, salpingitis, endometritis, cervicitis, vaginitis, vulvitis, orchitis, epididymitis, prostatitis, seminal vesicle cystitis, balanitis, posthitis, chorioamnionitis, funisitis, omphalitis, hepatitis, ascending cholangitis, cholecystitis, pancreatitis, peritonitis, hypophysitis, thyroiditis, parathyroiditis, adrenalitis, lymphangitis and lymphadenitis. In particular, examples of inflammatory diseases include pancreatitis.

Specific examples of the disease also include, cachexia and age-related diseases. Examples of age-related diseases include flail (infirmity), sarcopenia and locomotive syndrome. All of cachexia and these age-related diseases may also be inflammatory diseases.

Examples of the detection of the risk in a subject include: the determination of whether or not the subject is at risk; and the determination of whether the risk in the subject is high or low.

Examples of the detection of the presence or absence of a disease include: the determination of whether or not there is a likelihood that the subject has already developed the disease at present; and the determination of whether the likelihood that the subject has already developed the disease at present is high or low. Examples of the detection of the risk of developing a disease include: the determination of whether or not there is a likelihood that the subject will develop the disease in the future or a likelihood that the disease will be severe if the subject were to develop the disease in the future is high or low; and the determination of whether the likelihood that the subject will develop the disease in the future or the likelihood that the disease will be severe if the subject were to develop the disease in the future is high or low. Examples of the detection of the degree of progression of a disease include the determination of whether the degree of progression of the disease (such as the degree of severity) in the subject at present is high or low. Examples of the detection of the degree of progression of aging include the determination of whether the degree of progression of aging (such as the degree of severity) in the subject at present is high or low.

That is, the expression that a "subject is at risk" may mean, for example, that there is a likelihood that the subject has already developed a disease at present, that there is a likelihood that the subject will develop the disease in the future, and/or that there is a likelihood that the disease will be severe if the subject were to develop the disease in the future. The expression that a "subject is not at risk" may mean, for example, that there is no likelihood that the subject has already developed a disease at present, that there is no likelihood that the subject will develop the disease in the future, and/or that there is no likelihood that the disease will be severe if the subject were to develop the disease in the future. The expression that a "subject is at a high risk" may mean, for example, that there is a high likelihood that the subject has already developed a disease at present, that there is a high likelihood that the subject will develop the disease in the future, that there is a high likelihood that the disease will be severe if the subject were to develop the disease in the future, that the degree of progression of the disease in the subject at present is high, and/or that the degree of progression of aging in the subject at present is high. The expression that a "subject is at a low risk" may mean, for example, that there is a low likelihood that the subject has already developed a disease at present, that there is a low likelihood that the subject will develop the disease in the future, that there is a low likelihood that the disease will be severe if the subject were to develop the disease in the future, that the degree of progression of the disease in the subject at present is low, and/or that the degree of progression of aging in the subject at present is low.

The detection step can be carried out, for example, using as an indicator, the level of the value of the separation data (namely, whether the value of the separation data is high or low). The level of the value of the separation data can be determined, for example, by comparing the value of the separation data with a predetermined threshold value. In other words, the detection step may include, for example, the step of comparing the value of the separation data with a threshold value. That is, the expression that "the value of the separation data is high" may mean, for example, that the value of the separation data is high relative to a threshold value. The expression that "the value of the separation data is high relative to a threshold value" may mean, for example, that the value of the separation data is equal to or higher than the threshold value, that the value of the separation data is higher than the threshold value, or that the value of the separation data is statistically significantly higher than the threshold value. The expression that "the value of the separation data is high relative to a threshold value" may specifically mean, for example, that the value of the separation data is 1.01 times or more, 1.02 times or more, 1.03 times or more, 1.05 times or more, 1.07 times or more, 1.1 times or more, 1.2 times or more, 1.3 times or more, 1.5 times or more, 1.7 times or more, 2 times or more, 2.5 times or more, or 3 times or more the threshold value. Further, the expression that "the value of the separation data is low" may mean, for example, that the value of the separation data is low relative to a threshold value. The expression that "the value of the separation data is low relative to a threshold value" may mean, for example, that the value of the separation data is equal to or lower than the threshold value, that the value of the separation data is less than the threshold value, or that the value of the separation data is statistically significantly lower than the threshold value. The expression that "the value of the separation data is low relative to a threshold value" may specifically mean, for example, that the value of the separation data is 0.99 times or less, 0.98 times or less, 0.97 times or less, 0.95 times or less, 0.93 times or less, 0.9 times or less, 0.85 times or less, 0.8 times or less, 0.7 times or less, 0.6 times or less, 0.5 times or less, 0.4 times or less, or 0.3 times or less the threshold value.

The value of the separation data may be classified, for example, into "severe range" based on a threshold value. The value of the separation data may be classified, for example, into "non-severe range" based on the threshold value. The values of the separation data may specifically be classified, for example, into the severe range and the non-severe range, based on the threshold value. The term "severe range" may mean that any value of the separation data falling within this range indicates that there is high likelihood that the subject is at risk. The term "non-severe range" may mean that any value of the separation data falling within this range indicates that there is high likelihood that the subject is not at risk. That is, when the value of the separation data is within the severe range, it may be determined that the subject is at risk or at a high risk. On the other hand, when the value of the separation data is within the non-severe range, it may be determined that the subject is not at risk or at a low risk.

For example, in cases where the value(s) of the peak area (such as peak area %) and/or the peak height (such as peak height %) of the first peak and/or the second peak is/are high, it may be determined that the subject is at risk or at a high risk. Specifically, for example, in cases where the value(s) of the peak area (such as peak area %) and/or the peak height (such as peak height %) of the first peak and/or the second peak is/are high relative to a threshold value(s), it may be determined that the subject is at risk or at a high risk. In this case, the range(s) of the value(s) regarded as high relative to the threshold value(s) may be the severe range(s). More specifically, for example, in cases where the first peak area % is 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, or 30% or more, it may be determined that the subject is at risk or at a high risk. Further, it may be determined that the higher the value(s) of the peak area (such as peak area %) and/or the peak height (such as peak height %) of the first peak and/or the second peak, the higher the risk of the subject.

For example, in cases where the value(s) of the peak area (such as peak area %) and/or the peak height (such as peak height %) of the first peak and/or the second peak is/are low, it may be determined that the subject is not at risk or at a low risk. Specifically, for example, in cases where the value(s) of the peak area (such as peak area %) and/or the peak height (such as peak height %) of the first peak and/or the second peak is/are low relative to a threshold value(s), it may be determined that the subject is not at risk or at a low risk. In this case, the range(s) of the value(s) regarded as low relative to the threshold value(s) may be the non-severe range(s). More specifically, for example, in cases where the first peak area % is 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, or 9% or less, it may be determined that the subject is not at risk or at a low risk. Further, it may be determined that the lower the value(s) of the peak area (such as peak area %) and/or the peak height (such as peak height %) of the first peak and/or the second peak, the lower the risk of the subject.

For example, in cases where the value(s) of the peak area (such as peak area %) and/or the peak height (such as peak height %) of the third peak is/are low, it may be determined that the subject is at risk or at a high risk. Specifically, for example, in cases where the value(s) of the peak area (such as peak area %) and/or the peak height (such as peak height %) of the third peak is/are low relative to a threshold value(s), it may be determined that the subject is at risk or at a high risk. In this case, the range(s) of the value(s) regarded as low relative to the threshold value(s) may be the severe range(s). Further, it may be determined that the lower the value(s) of the peak area (such as peak area %) and/or the peak height (such as peak height %) of the third peak, the higher the risk of the subject.

For example, in cases where the value(s) of the peak area (such as peak area %) and/or the peak height (such as peak height %) of the third peak is/are high, it may be determined that the subject is not at risk or at a low risk. Specifically, for example, in cases where the value(s) of the peak area (such as peak area %) and/or the peak height (such as peak height %) of the third peak is/are high relative to a threshold value(s), it may be determined that the subject is not at risk or at a low risk. In this case, the range(s) of the value(s) regarded as high relative to the threshold value(s) may be the non-severe range(s). Further, it may be determined that the higher the value(s) of the peak area (such as peak area %) and/or the peak height (such as peak height %) of the third peak, the lower the risk of the subject.

When the separation data in which the first peak is taken as the target peak is used as an indicator, the risk to be detected may be selected, for example, from the risk of symptoms other than pancreatitis. When the separation data in which the second peak is taken as the target peak is used as an indicator, the risk to be detected may be selected, for example, from the risk of aging. When the separation data in which the third peak is taken as the target peak is used as an indicator, the risk to be determined may be selected, for example, from the risk of pancreatitis.

It is noted herein that the expression "to determine whether a subject is at risk, not at risk, at a high risk or at a low risk, in cases where certain separation data satisfies a certain standard (for example, when the value of the data is low or high, or within a certain range)" means to determine whether the subject is at risk, not at risk, at a high risk or at a low risk, at least to the extent that the above described standard is satisfied, and it is not required to determine the risk in the subject when the standard is not satisfied. In one embodiment, however, in the case of "determining whether a subject is at risk, not at risk, at a high risk or at a low risk, in cases where certain separation data satisfies a certain standard (for example, when the value of the data is low or high, or within a certain range)", it may be determined whether the subject is at risk, not at risk, at a low risk or at a high risk respectively, when the standard is not satisfied.

The "threshold value" can be set as appropriate by those skilled in the art, for example, depending on various conditions, such as the type of the separation data and the desired determination accuracy. The threshold value may be set, for example, for each of the symptoms to de determined, such as the symptoms of diseases and aging. The means for determining the threshold value is not particularly limited. The threshold value can be determined, for example, in accordance with a known technique used for data analysis for dividing a population into two groups.

The threshold value can be determined, for example, based on the value of separation data of an antibody sample obtained from a control subject. The separation data of an antibody sample obtained from a control subject is also referred to as "control separation data". The control separation data may be used in the detection step, by being used in the determination of the threshold value. Specifically, the control separation data may be used in the comparison with the separation data, by being used in the determination of the threshold value. In other words, the detection step may include, for example, the step of comparing the separation data with the control separation data.

The control subject may be, for example, a positive control or a negative control. The term "positive control" may refer to a subject that can be determined to be at risk or at a high risk. The term "negative control" may refer to a subject that can be determined to be not at risk or at a low risk. The positive control may be, for example, an individual that is affected by any of the above exemplified diseases (particularly, the same disease as the disease whose risk is to be detected), an individual that had once been affected by the disease, an individual with advanced aging, or an individual with a combination of such features. The negative control may be, for example, an individual that is not affected by any of the above exemplified diseases (particularly, the same disease as the disease whose risk is to be detected), an individual that had never been affected by the disease, an individual whose aging is not advanced, or an individual with a combination of such features. The threshold value may be determined based only on the value of the separation data measured for the positive control, may be determined based only on the value of the separation data measured for the negative control, or may be determined based on the values of the separation data measured for both the positive control and the negative control. In general, the threshold value may be determined based on the values of the separation data measured for both the positive control and the negative control. The numbers of the positive and negative controls are not particularly limited, as long as a threshold value which enables to determine the risk at a desired accuracy can be obtained. The numbers of the positive and negative controls may each be one person, or two or more persons. In general, the numbers of the positive and negative controls may each be a plurality of persons. The numbers of the positive and negative controls may each be, for example, five persons or more, 10 persons or more, 20 persons or more, or 50 persons or more. The numbers of the positive and negative controls may each be, for example, 10,000 persons or less, 1,000 persons or less, or 100 persons or less.

In cases where the threshold value is determined based only on the values of the separation data measured for the positive controls, for example, a value selected from the range from the upper limit to the lower limit of the values of the separation data measured for a plurality of individuals of the positive controls, such as the mean value, may be set as the threshold value. Alternatively, for example, the threshold value may be determined such that, in the distribution of the values of the separation data measured for a plurality of individuals of the positive controls, a predetermined proportion of the positive controls are included in the severe range. The predetermined proportion may be, for example, 70% or more, 80% or more, 90% or more, 95% or more, 97% or more, or 100%.

In cases where the threshold value is determined based only on the values of the separation data measured for the negative controls, for example, a value selected from the range from the upper limit to the lower limit of the values of the separation data measured for a plurality of individuals of the negative controls, such as the mean value, may be set as the threshold value. Alternatively, for example, the threshold value may be determined such that, in the distribution of the values of the separation data measured for a plurality of individuals of the negative controls, a predetermined proportion of the negative controls are included in the non-severe range. The predetermined proportion may be, for example, 70% or more, 80% or more, 90% or more, 95% or more, 97% or more, or 100%.

In cases where the threshold value is determined based on both the values of the separation data measured for the positive controls and the values of the separation data measured for the negative controls, the threshold value may be determined, for example, such that a predetermined proportion of the positive controls are included in the severe range, and a predetermined proportion of the negative controls are included in the non-severe range. The proportion of the positive controls included in the severe range, and the proportion of the negative controls included in the non-severe range are both the higher the more preferred. These proportions may each be, for example, 70% or more, 80% or more, 90% or more, 95% or more, 97% or more, or 100%. When it is difficult to increase both of these proportions, the threshold value may be set, for example, such that either one of the proportions is preferentially increased depending on various conditions, such as the purpose of use of the determination result obtained by the method according to the present invention. For example, in order to decrease the false-negative rate, the threshold value may be set such that the proportion of the positive controls included in the severe range is preferentially increased.

The determination of the threshold value may be carried out, for example, using software. For example, statistical analysis software may be used to determine a threshold value which allows for distinguishing between the negative controls and the positive controls, in the most statistically appropriate manner. Examples of such software include statistical analysis software such as "R".

Examples of the control subject also include the target subject oneself. That is, the risk in a subject may be determined, for example, using as an indicator a change in the separation data of the subject. The definition of the expression "the value of the separation data is high" may include the case in which the value of the separation data has increased. The expression "the value of the separation data has increased" may specifically mean that the value of the separation data has increased compared to a value in the past. Further, the definition of the expression "the value of the separation data is low" may include the case in which the value of the separation data has decreased. The expression "the value of the separation data has decreased" may specifically mean that the value of the separation data has decreased compared to a value in the past. That is, the threshold value may be, for example, a value in the past. The term "value in the past" refers to the value of the separation data of an antibody sample obtained from the target subject in a certain time point in the past. The target subject in a certain time point in the past may be, for example, a positive control or a negative control.

In cases where a change in the separation data of a subject is used as an indicator, an increase or decrease in the risk in the subject may be determined. The definition of the expression "to be at risk or at a high risk" may include the case in which the risk has increased. The expression "the risk has increased" may mean, specifically, that the risk has increased as compared to a certain time point in the past. Further, the definition of the expression "to be not at risk or at a low risk" may include the case in which the risk has decreased. The expression "the risk has decreased" may mean, specifically, that the risk has decreased as compared to a certain time point in the past.

It is noted that the definition of the expression "to obtain certain separation data so as to be used as an indicator for detecting the risk" is not limited to the case of obtaining the value itself of the separation data so as to be used as the indicator for detecting the risk, and also includes the case of obtaining another value that reflects the value of the separation data so as to be used as the indicator for the detection. For example, when the elution peaks are composed of the first to fourth peaks, the definition of the expression "to obtain the peak area % of the first peak so as to be used as an indicator for detecting the risk" is not limited to the case of obtaining the value itself of the peak area % of the first peak so as to be used as the indicator for detecting the risk, and also includes the case of obtaining another value that reflects the value of the peak area % of the first peak, such as the total value of the peak area % of the second to fourth peaks, so as to be used as the indicator for the detection. In either case, the numerical value to be used for the detection of the risk, such as a measured value or a threshold value, is corrected as appropriate depending on the type of the separation data, before being used. For example, in cases where the elution peaks are composed of the first to fourth peaks, the relationship "X=100%−Y" is established, when the value of the peak area % of the first peak is defined as X, and the total value of the peak area % of the second to fourth peaks is defined as Y. Accordingly, in cases where the total value of the peak area % of the second to fourth peaks (namely, "Y") is used as an indicator for detecting the risk, instead of the value itself of the peak area % of the first peak (namely, "X"), the expression "X satisfies a certain standard (for example, the value of X is low or high, or within a certain range)" is understood as "the value corrected by Y (namely, "100%−Y") satisfies the standard".

The detection result of the risk may be used as an indicator for determining whether or not to perform a treatment for reducing the risk (hereinafter, also referred to as a "risk reduction treatment") on the subject. In other words, it is possible to obtain an indicator for determining whether or not to perform a risk reduction treatment on a subject, by carrying out the detection method according to the present invention. That is, when it is determined by the detection method according to the present invention that a subject is at risk or at a high risk, for example, it may be determined to perform a risk reduction treatment on the subject. The detection method according to the present invention may be used, for example, singly, or in combination with other means, as an indicator(s) for determining whether or not to perform a risk reduction treatment on the subject. For example, it may be determined to carry out a risk reduction treatment on a subject, after having performed a definitive diagnosis by other means for the symptom the subject has been determined to be at risk or at a high risk by the detection method according to the present invention. The risk reduction treatment may be a medical practice or a non-medical practice. Examples of the risk reduction treatment include preventing or treating any of the diseases and aging as exemplified above. That is, the present invention may provide, for example, a method for preventing or treating a symptom of a disease, aging or the like. The prevention or treatment method may be, for example, a method for preventing or treating a symptom of a disease, aging or the like, the method including: the step of performing the detection method according to the present invention, and the step of performing prevention or treatment on a subject, when the subject is determined to be at risk or at a high risk by the detection method according to the present invention. Specifically, the prevention or treatment may be performed for the symptom the subject has been determined to be at risk or at a high risk by the detection method according to the present invention. The prevention or treatment can be performed, for example, by general means (such as medication and/or surgery) for each symptom.

Specific examples will be described below.

The method according to the present invention enables, for example, to separate an antibody of a subject based on the sugar chain structure characteristic of the risk of a symptom of a specific disease, aging or the like, to obtain separation data, and to easily detect such a risk by comparing the thus obtained data with separation data as a reference. Further, it is possible to monitor the process of treatment of a disease, or to determine the policy for the treatment, by obtaining separation data before and/or after performing some kind of treatment (such as mediation or surgery) for the disease, and comparing the obtained data with separation data as a reference. Examples of the separation data as a reference include separation data of a control subject. Specific examples of the separation data as a reference include: separation data of the same subject at another time point (such as the time point at which the subject is healthy or at which the subject has already developed the same disease); separation data of a healthy individual; separation data of a different patient that has developed the same disease; and separation data which is used as a reference when classifying into two or more groups in which the difference in the response to the above described treatment is observed.

For example, it is possible to evaluate the risk, such as the risk of having some kind of disease and/or the risk of developing the disease, in a subject, by taking separation data of a healthy individual (model) as model separation data, and comparing the separation data of the subject with the model separation data. Further, it is possible to extract the difference in sugar chain patterns between antibodies of the healthy individual (model) and the subject, by fractionating the fraction(s) of the peak(s) responsible for the difference in the separation data between the model and the subject. It is also possible to perform the monitoring of a disease of a patient, by taking separation data of the patient oneself at a certain time point as model separation data, and comparing the model separation data with separation data of the same patient at another time point. In the case of comparing two different specimen groups, the statistical probability (P value) can be used to evaluate whether or not the difference between the separation data obtained from the above described two different specimen groups is a significant difference. It is said that a lower P value indicates that the above described evaluation result is more significant, and when the P value is less than the significance level, it can be said that the above described evaluation result shows a statistically significant difference. The significance level is usually 5%.

Examples of the characteristic of a sugar chain structure related to a specific disease include: the presence or absence of the addition of sialic acid; and the difference in the amount of sialic acid added. Particularly, in patients with rheumatism, it is known that the amounts of sialic acid and galactose added to an antibody(ies) are decreased. Therefore, it is possible to easily evaluate the presence or absence and the contents of sialic acid and galactose, as well as the difference from healthy individuals, based on the difference in the interaction with an Fc-binding protein. Further, according to the method according to the present invention, an antibody can be separated into groups of antibody molecules having different sugar chain structures based on the Fc-binding function, without identifying the individual sugar chain structures. That is, the method according to the present invention enables to extract a characteristic(s) as separation data, based on the Fc-binding function as an entirety of particular sugar chain structures, which function has not been clarified by previously known correlations between the binding amounts of sialic acid and galactose with diseases. Therefore, it is possible to evaluate the risk, such as the risk of the presence or absence of a disease or the risk of developing the disease at a high accuracy.

The type of sugar chains which bind to IgG are partially controlled by antibody-producing B cells. Since it has been reported in Non-patent Document (Mol. Cell. Proteom., 10, M110.004655 (2011)) that cytokines cause changes in sugar chain modifications, it is also possible to evaluate the secretion of the cytokines based on the pattern of sugar chains which bind to IgG. Cytokines are substances released from cells, and are related to various diseases. For example, it is known that the secretion of proinflammatory cytokines such as IL-6 and TNF-α is increased associated with aging, and leads to a decrease in motor and cognitive functions, such as flail (infirmity) and sarcopenia. The method according to the present invention also enables to evaluate the risk of developing any of these age-related diseases. Further, since proinflammatory cytokines which are released associated with malignant tumors cause debilitated conditions (cachexia), such as weight loss in cancer patients, the method according to the present invention is a useful method also in the case of evaluating cachexia.

Since the strength of the affinity of an antibody to the Fc-binding protein of the present invention has an impact on the activity of immune cells, such as natural killer cells, monocytes and macrophages that have an injurious or phagocytosis effect on a binding substance to which the antibody is bound, it is possible to evaluate the risk of developing a disease affected by the injurious or phagocytosis effect of natural killer cells, monocytes and macrophages, by detecting the difference in the above described affinity. Examples of the disease include cancer, autoimmune diseases, infectious diseases, allergies and inflammatory diseases. Examples of infectious diseases include opportunistic infectious diseases. Opportunistic infectious diseases are infectious diseases caused by pathogens that usually do not cause infections in healthy individuals. Examples of pathogens include viruses, bacteria, fungi and protozoa. Further, the effect of activating immune cells by an antibody acquired due to vaccination or being affected by the disease, can also be evaluated based on the strength of the affinity of the antibody to the Fc-binding protein. By measuring the affinity of the acquired antibody to the Fc-binding protein, in addition to measuring the amount of the antibody in blood, it is also possible to predict the risk of developing an infectious disease at a high accuracy.

<2> Antibody Mixture

The present invention provides an antibody mixture having a specific composition. This antibody mixture is also referred to as "the antibody mixture according to the present invention". The antibody mixture according to the present invention can be produced, for example, by the antibody production method according to the present invention. The antibody mixture according to the present invention can be produced, for example, as an eluted fraction containing antibodies.

Examples of the antibody mixture according to the present invention include a composition containing two or more types of antibodies, wherein the composition satisfies two or more (for example, two, three, four, five, six, seven, eight or nine) items of the following I to IX:

I. the value obtained by dividing the content of an antibody(ies) having G1Fa by the content of an antibody(ies) having G0F is 0.4 or less, in weight ratio;

II. the value obtained by dividing the content of an antibody(ies) having G2F by the content of the antibody(ies) having G0F is 0.2 or less, in weight ratio;

III. the value obtained by dividing the content of an antibody(ies) having G2F+2SA by the content of the antibody(ies) having G0F is 0.03 or less, in weight ratio;

IV. the value obtained by dividing the content of an antibody(ies) having G1Fb by the content of the antibody(ies) having G1Fa is 0.5 or more, in weight ratio;

V. the value obtained by dividing the content of the antibody(ies) having G2F by the content of the antibody(ies) having G1Fb is 0.6 or less, in weight ratio;

VI. the value obtained by dividing the content of an antibody(ies) having G2F+SA by the content of the antibody(ies) having G1Fb is 0.3 or less, in weight ratio;

VII. the value obtained by dividing the content of the antibody(ies) having G2F+2SA by the content of the antibody(ies) having G1Fb is 0.12 or less, in weight ratio;

VIII. the ratio of the content of an antibody(ies) having G2+SA to the total content of the antibodies is 0.2% or less, in weight ratio; and IX. the ratio of the content of an antibody(ies) having G2+2SA to the total content of the antibodies is 0.2% or less, in weight ratio.

Examples of the antibody mixture according to the present invention also include a composition containing two or more types of antibodies, wherein the composition satisfies two or more (for example, two, three, four, five, six, seven, eight or nine) items of the following I to IX:

I. the value obtained by dividing the content of an antibody(ies) having G1Fa by the content of an antibody(ies) having G0F is 1.8 or more, in weight ratio;

II. the value obtained by dividing the content of an antibody(ies) having G2F by the content of the antibody(ies) having G0F is 0.6 or more, in weight ratio;

III. the value obtained by dividing the content of an antibody(ies) having G2F+2SA by the content of the antibody(ies) having G0F is 0.06 or more, in weight ratio;

IV. the value obtained by dividing the content of an antibody(ies) having G1Fb by the content of the antibody(ies) having G1Fa is 0.3 or less, in weight ratio;

V. the value obtained by dividing the content of the antibody(ies) having G2F by the content of the antibody(ies) having G1Fb is 3.0 or more, in weight ratio;

VI. the value obtained by dividing the content of an antibody(ies) having G2F+SA by the content of the antibody(ies) having G1Fb is 0.6 or more, in weight ratio;

VII. the value obtained by dividing the content of the antibody(ies) having G2F+2SA by the content of the antibody(ies) having G1Fb is 0.3 or more, in weight ratio;

VIII. the ratio of the content of an antibody(ies) having G2+SA to the total content of the antibodies is 2% or more, in weight ratio; and IX. the ratio of the content of an antibody(ies) having G2+2SA to the total content of the antibodies is 0.6% or more, in weight ratio.

The descriptions of the sugar chain structures in the above described items are as shown in FIG. 3 and FIG. 4.

The applications of the antibody mixture according to the present invention are not particularly limited. The antibody mixture according to the present invention can be used, for example, in a diagnostic application. The diagnostic application may be, for example, the detection of the risk (namely, the presence or absence of a disease, the risk of developing a disease, the degree of progression of a disease and/or the degree of progression of aging) in a subject. That is, in cases where the antibody mixture according to the present invention is one obtained by separating antibodies obtained from a subject by the separation method according to the present invention or the like, the risk in the subject can be detected using data of the separation pattern of the antibodies, which data are obtained upon obtaining the antibody mixture according to the present invention, as an indicator. Further, the patterns of sugar chain structures in the antibody mixture according to the present invention may also be used as indicators to detect the risk in the subject.

EXAMPLES

The present invention will now be described in more specific detail, with reference to non-limiting Examples.
Preparation of Fc-Binding Protein-Immobilized Gel

Example 1 Preparation of Val 176-Amino Acid Substitution Product of FcR9

An amino acid substitution was introduced into FcR9 (SEQ ID NO: 2) prepared in accordance with the method disclosed in WO 2015/199154, to prepare an Fc-binding protein in which the 176th valine (Val at amino acid number 176 of the amino acid sequence of SEQ ID NO: 1) was substituted with phenylalanine. Specifically, an amino acid substitution was introduced into plasmid pET-FcR9 (disclosed in WO 2015/199154) containing a polynucleotide (SEQ ID NO: 3) encoding FcR9, by PCR, to prepare an Fc-binding protein in which Val 176 in the FcR9 was substituted with phenylalanine.

FcR9 (SEQ ID NO: 2) is an Fc-binding protein in which the 43rd Val was substituted with Glu (corresponding to the 27th position in SEQ ID NO: 1), the 45th Phe was substituted with Ile (corresponding to the 29th SEQ ID NO: 1), the 51st Tyr was substituted with Asn (corresponding to the 35th position in SEQ ID NO: 1), the 64th Gln was substituted with Arg (corresponding to the 48th position in SEQ ID NO: 1), the 91st Phe was substituted with Leu (corresponding to the 75th position in SEQ ID NO: 1), the 108th Asn was substituted with Ser (corresponding to the 92nd position in SEQ ID NO: 1), the 133rd Val was substituted with Glu (corresponding to the 117th position in SEQ ID NO: 1), the 137th Glu was substituted with Gly (corresponding to the 121th position in SEQ ID NO: 1) and the 187th Phe was substituted with Ser (corresponding to the 171th position in SEQ ID NO: 1), in an Fc-binding protein containing a wild type FcγRIII extracellular region shown in SEQ ID NO: 4.

The method for preparing each Fc-binding protein will be described below in detail.

(1) In order to substitute the 176th valine of the Fc-binding protein (namely, Val at amino acid number 176 of the amino acid sequence of SEQ ID NO: 1) with phenylalanine, a reaction liquid having the same composition as that shown in Table 1 was prepared, using as a template, the plasmid pET-FcR9 (disclosed in WO 2015/199154) containing a polynucleotide (SEQ ID NO: 3) encoding FcR9 (SEQ ID NO: 2) which had been prepared in accordance with the method disclosed in WO2015/199154, and using oligo primers consisting of the sequences of SEQ ID NO: 5 (5'-TAATACGACTCACTATAGGG-3') and SEQ ID NO: 6 (5'-CATTTTTGCTGCCGAACAGCCCACGGCAGG-3'). Thereafter, the thus prepared reaction liquid was heat-treated at 95° C. for 2 minutes, and PCR was performed by 30 cycles of a reaction, each cycle consisting of: the first step at 95° C. for 30 seconds; the second step at 50° C. for 30 seconds; and the third step at 72° C. for 90 seconds; followed by heat treatment at 72° C. for 7 minutes. The resulting PCR product was designated as V176p1.

TABLE 1

| Composition | Amount |
| --- | --- |
| Template DNA | 2 μL |
| 10 μM Forward primer | 1 μL |
| 10 μM Reverse primer | 1 μL |
| 5 × PrimeSTAR buffer (manufactured by Takara Bio Inc.) | 4 μL |
| 2.5 mM dNTPs | 2 μL |
| 2.5 U/μL PrimeSTAR HS (manufactured by Takara Bio Inc.) | 0.5 μL |
| H$_2$O | up to 20 μL |

(2) A reaction liquid having the same composition as that shown in Table 1 was prepared, using as a template, the plasmid pET-FcR9 (disclosed in WO 2015/199154) containing a polynucleotide (SEQ ID NO: 3) encoding FcR9 (SEQ ID NO: 2) which had been prepared in accordance with the method disclosed in WO2015/199154, and using oligo primers consisting of the sequences of SEQ ID NO: 7 (5'-TATGCTAGTTATTGCTCAG-3') and SEQ ID NO: 8 (5'-cctgccgtgggctgTTCGGCAGCAAAAATG-3'). Thereafter, the thus prepared reaction liquid was heat-treated at 95° C. for 2 minutes, and PCR was performed by 30 cycles of a reaction, each cycle consisting of: the first step at 95° C. for 30 seconds; the second step at 50° C. for 30 seconds; and the third step at 72° C. for 90 seconds; followed by heat treatment at 72° C. for 7 minutes. The resulting PCR product was designated as V176p2.

(3) The two types of PCR products obtained in (1) and (2) (V176p1 and V176p2) were mixed, to prepare a reaction liquid having the composition shown in Table 2. The thus prepared reaction liquid was heat-treated at 98° C. for 5 minutes, and then PCR was performed by 5 cycles of a reaction, each cycle consisting of: the first step at 98° C. for 10 seconds; the second step at 55° C. for 5 seconds; and the third step at 72° C. for 1 minute; to obtain a PCR product V176p in which V176p1 and V176p2 were joined to each other.

TABLE 2

| Composition | Amount |
| --- | --- |
| PCR product | each 2 μL |
| 2.5 U/μL PrimeSTAR HS (manufactured by Takara Bio Inc.) | 0.5 μL |
| 5 × PrimeSTAR buffer (manufactured by Takara Bio Inc.) | 4 μL |
| 2.5 mM dNTPs | 2 μL |
| H$_2$O | up to 20 μL |

(4) PCR was carried out using the PCR product V176p obtained in (3) as a template, and using oligonucleotides consisting of the sequences of SEQ ID NOs: 5 and 7 as PCR primers. After preparing a reaction liquid having the composition shown in Table 3, the reaction liquid was heat-treated at 98° C. for 5 minutes, and PCR was performed by 30 cycles of a reaction, each cycle consisting of: the first step at 98° C. for 10 seconds; the second step at 55° C. for 5 seconds; and the third step at 72° C. for 1 minute. As a result, a polynucleotide encoding an Fc-binding protein in which the 176th amino acid of the Fc-binding protein (FcR9) was substituted with phenylalanine, was obtained. The resulting polynucleotide was designated as V176p3.

TABLE 3

| Composition | Amount |
| --- | --- |
| PCR product | 2 μL |
| 10 μM Forward primer | 2 μL |
| 10 μM Reverse primer | 2 μL |
| 5 × PrimeSTAR buffer (manufactured by Takara Bio Inc.) | 10 μL |
| 2.5 mM dNTPs | 4 μL |
| 2.5 U/μL PrimeSTAR HS (manufactured by Takara Bio Inc.) | 1 μL |
| H₂O | up to 50 μL |

(5) The polynucleotide obtained in (4) was purified, and then digested with restriction enzymes NcoI and HindIII. The resultant was then ligated to an expression vector pETMalE (JP 2011-206046 A) which had been digested with restriction enzymes NcoI and HindIII, in advance. Thereafter, the resulting ligation product was used to transform *Escherichia coli* BL21 (DE3) strain (manufactured by Nippon Gene Co., Ltd.).

(6) The resulting transformants were cultured in LB culture medium supplemented with 50 μg/mL of kanamycin. Plasmids were extracted from the collected bacterial cells (transformants).

(7) A cycle sequence reaction was performed using a BigDye Terminator v3.1 Cycle Sequencing Kit (manufactured by Life Technologies Corporation) based on the chain terminator method, and the nucleotide sequence of the polynucleotide encoding human FcγRIIIa and the surrounding region thereof in the resulting plasmid was analyzed by a fully automatic DNA sequencer, Applied Biosystems 3130 Genetic Analyzer (manufactured by Life Technologies Corporation). In the above described analysis, an oligonucleotide consisting of the sequence of SEQ ID NO: 5 (5'-TAATACGACTCACTATAGGG-3') or SEQ ID NO: 7 (5'-TATGCTAGTTATTGCTCAG-3') was used as a sequencing primer. The results of the sequence analysis confirmed that transformants expressing an Fc-binding protein (SEQ ID NO: 9) in which the Val 176 in the Fc-binding protein FcR9 was substituted with Phe were obtained.

Example 2 Preparation of Fc-Binding Protein to which Cysteine Tag was Added (FcR9_F_Cys)

(1) PCR was carried out using, as a template, an expression vector pET-FcR9_F containing a polynucleotide of SEQ ID NO: 10 which encodes the amino acid sequence of SEQ ID NO: 9 prepared in Example 1. As the primers to be used in the above described PCR, oligonucleotides consisting of the sequences of SEQ ID NO: 11 (5'-TAGC-CATGGGCATGCGTACCGAAGATCTGCCGAAAGC-3') and SEQ ID NO: 12 (5'-CCCAAGCT-TATCCGCAGGTATCGTTGCGGCACCCTTGGGTAA-TGGTAATA TTCACGGTCTCGCTGC-3') were used. After preparing a reaction liquid having the composition shown in Table 3, the reaction liquid was heat-treated at 98° C. for 5 minutes, and PCR was performed by 30 cycles of a reaction, each cycle consisting of: the first step at 98° C. for 10 seconds; the second step at 55° C. for 5 seconds; and the third step at 72° C. for 1 minute.

(2) The polynucleotide obtained in (1) was purified, and then digested with restriction enzymes NcoI and HindIII. The resultant was then ligated to an expression vector pTrc-PelBV3 prepared in accordance with the method disclosed in WO 2015/199154, which was digested with restriction enzymes NcoI and HindIII in advance. Thereafter, the resulting ligation product was used to transform *Escherichia coli* W3110 strain.

(3) The resulting transformants were cultured in LB culture medium supplemented with 100 μg/mL of carbenicillin, and then a QIAprep Spin Miniprep kit (manufactured by Quiagen Ltd.) was used to obtain an expression vector pTrc-FcR9_F_Cys.

(4) The analysis of the nucleotide sequence of the pTrc-FcR9_F_Cys was carried out in the same manner as in Example 1 (7), except that an oligonucleotide consisting of the sequence of SEQ ID NO: 13 (5'-TGTGGTATGGCTGTGCAGG-3') or SEQ ID NO: 14 (5'-TCGGCATGGGGTCAGGTG-3') was used as a sequencing primer.

The amino acid sequence of a polypeptide expressed by the expression vector pTrc-FcR9_F_Cys is shown in SEQ ID NO: 15, and the sequence of a polynucleotide encoding the polypeptide is shown in SEQ ID NO: 16. In the sequence of SEQ ID NO: 15, the region from the first methionine (Met) to the 22nd alanine (Ala) is an improved PeiB signal peptide, and the region from the 24th glycine (Gly) to the 199th glutamine (Gin) is the amino acid sequence of the Fc-binding protein (corresponding to the region from the 17th to 192nd residue of SEQ ID NO: 1), and the region from the 200th glycine (Gly) to the 207th glycine (Gly) is the cysteine tag sequence.

Example 3 Preparation of FcR9_F_Cys (1) The transformants expressing FcR9_F_Cys prepared in Example 2 were inoculated in 400 mL of 2YT liquid medium (16 g/L of peptone, 10 g/L of yeast extract and 5 g/L of sodium chloride) containing 100 μg/mL of carbenicillin and placed in a 2 L baffle flask, and aerobically cultured with shaking at 37° C. overnight, to perform preculture.

(2) A quantity of 180 mL of the culture fluid prepared in (1) was inoculated in 1.8 L of a liquid medium containing 10 g/L of glucose, 20 g/L of yeast extract, 3 g/L of trisodium phosphate dodecahydrate, 9 g/L of disodium hydrogen phosphate dodecahydrate, 1 g/L of ammonium chloride and 100 mg/L of carbenicillin, and a 3 L fermenter (manufactured by Biott Corporation) was used to perform main culture. The main culture was initiated under the conditions of a temperature of 30° C., a pH of from 6.9 to 7.1, an air flow rate of 1 VVM and a saturated dissolved oxygen concentration of 30%. The pH was controlled using 50% phosphoric acid as an acid and 14% ammonia water as an alkali, the dissolved oxygen concentration was controlled by changing the stirring rate, and the lower limit and the upper limit of the number of revolutions of the stirring were set to 500 rpm and 1,000 rpm, respectively. After the start of culturing, a feed medium (248.9 g/L of glucose, 83.3 g/L of yeast extract and 7.2 g/L of magnesium sulfate heptahydrate) was added while controlling the dissolved oxygen (DO) concentration, at the time point when the glucose concentration was unable to measure.

(3) When the absorbance at 600 nm (OD 600 nm), as an indicator of the amount of bacterial cells, had reached about 150, the culture temperature was lowered to 25° C. After confirming that the culture temperature had reached the set temperature, IPTG was added thereto to yield a final concentration of 0.5 mM, and the culture was continued at 25° C.

(4) The culture was terminated about 48 hours after the start of the culture, and the culture fluid was centrifuged at 4° C. and 8,000 rpm for 20 minutes, to collect bacterial cells (5) The thus collected bacterial cells were suspended in a 20 mM Tris-HCl buffer solution (pH 7.0) to yield a concentration of 5 mL/1 g (of bacterial cells). Thereafter, an ultrasonic wave generator (Insonator 201M (trade name), manufactured by Kubota corporation) was used to crush the bacterial cells at 4° C. and an output of about 150 W for about 10 minutes. The resulting crushed bacterial cell liquid was centrifuged twice at 4° C. and 8,000 rpm for 20 minutes, and the supernatant was collected.

(6) The supernatant obtained in (5) was applied to a VL 32×250 column (manufactured by Merck Millipore) which had been filled with 140 mL of TOYOPEARL CM-650M (manufactured by Tosoh Corporation) and equilibrated with a 20 mM phosphate buffer solution (8 mM sodium dihydrogen phosphate and 12 mM disodium hydrogen phosphate) (pH 7.0), in advance, at a flow velocity of 5 mL/min. After washing with the buffer solution used for the equilibration, the column was eluted with a 20 mM phosphate buffer solution (pH 7.0) containing 0.5M sodium chloride.

(7) The eluate obtained in (6) was applied to an XK 26/20 column (manufactured by GE Healthcare Inc.) which had been filled with 90 mL of IgG Sepharose (manufactured by GE Healthcare Inc.) and equilibrated with a 20 mM Tris-HCl buffer solution (pH 7.4) containing 150 mM sodium chloride, in advance. After washing with the buffer solution used for the equilibration, the column was eluted with a 0.1 M glycine hydrochloride buffer solution (pH 3.0). The pH of the eluate was adjusted around neutral, by adding a 1 M Tris-HCl buffer solution (pH 8.0) in an amount ¼ of the amount of the eluate.

About 20 mg of high-purity FcR9_F_Cys was obtained by the above described purification.

Example 4 Preparation of Fc-Binding Protein (FcR9_F)-Immobilized Gel and Separation of Antibody (1) Hydroxyl groups present on the surface of 2 mL of a hydrophilic vinyl polymer for use as a separation agent (a filler for liquid chromatography, manufactured by Tosoh Corporation) were activated with iodoacetyl groups, and thereafter, 4 mg of FcR9_F_Cys prepared in Example 3 was allowed to react with the polymer, to obtain an FcR9_F-immobilized gel.

(2) A stainless-steel column having a diameter of 4.6 mm and a length of 75 mm was filled with 1.2 mL of the FcR9_F-immobilized gel prepared in (1), to prepare an FcR9_F column.

(3) The FcR9_F column prepared in (2) was connected to a high-performance liquid chromatography apparatus (manufactured by Tosoh Corporation), and equilibrated with a 20 mM acetate buffer solution (pH 5.5) containing 50 mM sodium chloride, as an equilibration buffer.

(4) A quantity of 5 μL of a monoclonal antibody (Rituxan, a mouse-human chimeric antibody, manufactured by Nippon Zenyaku Kogyo Co., Ltd.), which had been diluted with PBS (Phosphate Buffered Saline) (pH 7.4) to yield a concentration of 1.0 mg/mL, was added to the column at a flow velocity of 0.6 mL/min.

(5) After washing the column with the equilibration buffer for 2 minutes, while maintaining a flow velocity of 0.6 mL/min, the adsorbed monoclonal antibody was eluted with a pH gradient using a 10 mM glycine hydrochloride buffer solution (pH 3.0) (namely, the gradient in which the concentration of the 10 mM glycine hydrochloride buffer solution (pH 3.0) reaches 100% in 28 minutes).

The result (elution pattern) is shown in FIG. 1. Since the monoclonal antibody interacts with the Fc-binding protein, the antibody was separated into a plurality of peaks, not a single peak as in the case of elution by gel filtration chromatography. The first peak with a shorter elution time was defined as peak A and the third peak with a longer elution time was defined as peak B.

Example 5 Separation of Human-Derived Antibody Using Fc-Binding Protein (FcR9_F)-Immobilized Gel The same procedure as in Example 4 was performed except that a human-derived gamma globulin preparation (manufactured by The Chemo-Sero-Therapeutic Research Institute) was used as an antibody. The separation pattern of the human-derived gamma globulin preparation was shown in FIG. 2. A separation pattern different from the separation result (FIG. 1) of the monoclonal antibody (Rituxan) used in Example 4 was obtained.

Further, peak C and peak D in FIG. 2, which are separation peaks characteristic of a human-derived antibody, were repeatedly fractionated, to obtain the human-derived antibody contained in the respective fractions.

Example 6 Structural Analysis of Sugar Chains of Monoclonal Antibody

The structural analysis of the sugar chains of the antibody contained in the peak A and peak B fractions separated in Example 4 was carried out in the same manner as the method disclosed in JP 2016-169197 A. The results are shown in FIG. 3 and Table 4. Man represents mannose, GlcNAc represents N-acetyl glucosamine, Gal represents galactose, Fuc represents fucose, and NeuAc represents -acetylneuraminic acid.

TABLE 4

| Abbreviations in FIG. 3 | peak A (composition percentage %) | peak B (composition percentage %) |
| --- | --- | --- |
| Man5 | 1.2 | Not Detect |
| G0 | 5.9 | 3.0 |
| G0F | 64.2 | 16.4 |
| G1Fa | 15.4 | 57.6 |
| G1Fb | 9.9 | 3.6 |
| G2F | 1.7 | 12.7 |
| G1F + SA | 0.2 | 0.9 |
| G2F + SA | 0.3 | 2.9 |
| G2F + 2SA | Not Detect | 1.6 |

Example 7 Structural Analysis of Sugar Chains of Human-Derived Antibody

The structural analysis of the sugar chains of the antibody contained in the peak C and peak D fractions fractionated in Example 5 was carried out in the same manner as in Example 6. The results of the structural analysis of the sugar chains of the antibody contained in the peak C and peak D fractions are shown in FIG. 4 and Table 5.

TABLE 5

| Abbreviations in FIG. 4 | peak C (composition percentage %) | peak D (composition percentage %) |
|---|---|---|
| G0 | 0.4 | 0.6 |
| G0F | 48.4 | 8.1 |
| G1/G0F + GN | 8.2 | 3.6 |
| G1Fa | 9.9 | 17.5 |
| G1Fb | 12.7 | 3.6 |
| G1F + GN | 2.1 | 4.1 |
| G2 | Not Detect | 2.9 |
| G2F | 5.8 | 18.1 |
| G1F + SA | 1.2 | 1.9 |
| G2F + SA | 2.6 | 23.6 |
| G2F + 2SA | 1.2 | 3.2 |
| G2F + GN | 0.9 | 1.8 |
| S1 | 0.8 | Not Detect |
| S2 | 2.5 | 2.3 |
| S3 | 1.5 | 2.4 |
| G2 + SA | Not Detect | 3.2 |
| G2 + 2SA | Not Detect | 0.8 |

The results of Example 6 and Example 7 have revealed, by using an FcR column filled with an Fc-binding protein-immobilized gel, that the presence or absence of galactose contributes to the separation of an antibody(ies) (based on the comparison of the composition percentage of G0F between peak A and peak B, and also on the comparison of those of G1F and G2F between these peaks, in Table 4. Each number shown between the abbreviations G and F represents the number of galactose), and likewise that the antibody(ies) are separated based on the presence or absence of sialic acid. Further, the comparison between FIG. 3 and FIG. 4 has revealed that human-derived gamma globulin has sugar chain structures specific to humans, different from a commercially available antibody drug, Rituxan, which is a mouse chimeric antibody. Among these sugar chain structures specific to humans, an antibody having sugar chain structures to which sialic acid is added can be used as an indicator for specific diseases. Therefore, the use of the method according to the present invention allows for easy measurement of diseases, early detection of abnormalities by comparison with healthy individuals, prognosis management of affected patients and the like.

Example 8 Separation of Human-Derived Antibodies Obtained from Individuals of Different Ages, Using Fc-Binding Protein (FcR9_F)-Immobilized Gel (1) Blood was collected from healthy individuals from whom informed consent had been obtained. The age and sex of the healthy individuals are shown below.
(Specimen A) 36 years old, female
(Specimen B) 44 years old, female
(Specimen C) 55 years old, female
(2) Serum obtained by centrifuging blood collected from each individual in (1) was purified using a gamma globulin G purification kit (manufactured by Thermo Fisher Scientific, Inc.) in which Protein G is immobilized on a solid phase, to obtain purified gamma globulin for each specimen.
(3) Using the gamma globulin obtained for each specimen in (2), the separation pattern of the gamma globulin was obtained in the same manner as in Example 4, except that the elution was carried out under the following conditions. After washing the column with the equilibration buffer for 5 minutes, while maintaining a flow velocity of 0.6 mL/min, the adsorbed gamma globulin was eluted with a pH gradient using a 10 mM glycine hydrochloride buffer solution (pH 3.0) (namely, the gradient in which the concentration of the 10 mM glycine hydrochloride buffer solution (pH 3.0) reaches 100% in 30 minutes).
(4) In each separation pattern obtained in (3), corresponding peaks were defined as the first peak, the second peak, the third peak and the fourth peak, in the order of from the peak appeared at a shorter elution time after the start of the pH gradient, and normalized taking the detected value of the third peak as 1.

The results of Example 8 are shown in FIG. 5. It can be seen from FIG. 5 that, as the age of the donor increases in the order of Specimen A, Specimen B and Specimen C, the proportion of gamma globulin eluted at a shorter elution time(s) is increased. In particular, it can be seen that the peak area % of the first peak and the second peak in Specimen C is increased, as compared to that in Specimen A and Specimen B. A larger proportion of gamma globulin eluted at a longer elution time means that the gamma globulin has a higher capacity to bind to natural killer cells, monocytes and macrophages, and that is capable of activating these cells. On the other hand, a larger proportion of gamma globulin eluted at a shorter elution time indicates that the effect of activating the above described cells is not sufficiently obtained, and that the risk of developing a disease which is affected by the activity of these cells is increased. Examples of such a disease include infectious diseases caused by viruses, bacteria and the like; cancer; allergies; and inflammatory diseases. It can be seen from the variation in the separation patterns of gamma globulin specimens in Example 8 that the risk of developing such a disease is increased with an increase in age.

Example 9 Separation of Human-derived Antibodies Obtained from Individuals of Different Ages, Using Fc-binding Protein-immobilized Gel (1) Blood was collected from healthy individuals from whom informed consent had been obtained. Age groups and the numbers of specimens of the healthy individuals are shown below.
From 18 to 29 years old: 23 specimens
From 30 to 39 years old: 21 specimens
From 40 to 49 years old: 21 specimens
From 50 to 59 years old: 24 specimens
From 60 to 75 years old: 15 specimens
(2) Serum obtained by centrifuging blood collected from each individual in (1) was diluted 10-fold with PBS, and then allowed to pass through a filter with a diameter of 0.2 μm (manufactured by Merck Millipore) to prepare each measurement sample.
(3) For each measurement sample obtained in (2), the separation pattern of gamma globulin was obtained in the same manner as in (3) in Example 8, except that 10 μL of the measurement sample was added at a flow velocity of 0.6 mL/min.
(4) In each separation pattern obtained in (3), corresponding peaks were defined as the first peak, the second peak, the third peak and the fourth peak, in the order of from the peak appeared at a shorter elution time after the start of the pH gradient. The area value of the first peak was divided by the total area value from the start until the end of the pH gradient, and the resulting value was defined as the first peak area %.

The results of Example 9 are shown in FIG. 6. It can be seen from FIG. 6 that the values of the first peak area % are significantly increased as the age of the donors increase in the order of from the specimens of individuals in their fifties and the specimens of individuals of 60 years old or higher, as compared to the specimens of individuals of younger than 50 years old, and thus that the proportion of the gamma globulin eluted at a shorter elution time is increased with an increase in age. Further, it can also be seen that specimens with a high first peak area % are present also in the specimens of individuals of younger than 50 years old, although in a low proportion. The above results reveal that the immune activity is decreased with aging when evaluated as a population, and also that the immune activity can decrease even in younger generation, when evaluated as an individual.

Example 10 Separation of Gamma Globulin Derived from Cancer Patients

The separation of gamma globulin was carried out in the same manner as in Example 9, except for using blood collected from healthy individuals as well as from patients with pancreatic cancer, gastric cancer and breast cancer, from whom informed consent had been obtained, and the first peak area % was determined for each specimen.

Example 11 Separation of Gamma Globulin Derived from Autoimmune Disease Patients The separation of gamma globulin was carried out in the same manner as in Example 9, except for using blood collected from patients with rheumatism and Sjogren's syndrome from whom informed consent had been obtained, and the first peak area % was determined for each specimen.

The results of Examples 10 and 11 are shown in FIG. 7 and FIG. 8, respectively. The values of the first peak area % were significantly higher in the specimens of patients with pancreatic cancer (Panel a of FIG. 7), gastric cancer (Panel b of FIG. 7), breast cancer (Panel c of FIG. 7), rheumatism (Panel a of FIG. 8) and Sjogren's syndrome (Panel b of FIG. 8), as compared to the specimens of healthy individuals. Further, it has been found out that the value of the first peak area % is increased corresponding to the stage of disease, in patients with cancer diseases. The stage of disease as used herein is that in accordance with the staging defined by Union for International Cancer Control (UICC). The above results indicate that the immune activity related to the Fc-binding protein is decreased in patients with cancer diseases and autoimmune diseases. In particular, the values of the first peak area % are markedly increased in patients with cancer diseases, indicating a great decrease in the immune activity. In a cancer disease or an autoimmune disease, it is considered that a decrease in the above described immune activity is a factor for developing the disease, or alternatively, that the development of the disease caused a decrease in the immune activity. Since the values of the first peak area % in the specimens of healthy individuals are different from the values in the specimens of patients with diseases, the first peak area % can be used for the diagnosis of the diseases. Further, since the values of the first peak area % vary corresponding to the stage of disease in cancer diseases, the first peak area % can also be used for the evaluation of the progression and the malignancy of cancer.

Example 12 Evaluation of Separation of Cancer Patient-Derived Gamma Globulin, Corrected with Age (1) The separation of gamma globulin was carried out in the same manner as in Example 9, except for using blood collected from patients with renal cancer and colorectal cancer from whom informed consent had been obtained, and the first peak area % was determined for each specimen.

(2) A correlation curve between the first peak area % determined by the measurement of the specimens of healthy individuals in Example 9, with age, was obtained by polynomial approximation, and the value calculated by introducing the age of each specimen into the formula of the correlation curve, was defined as the correction value.

(3) The value calculated in (2) was subtracted from the values of the first peak area % determined for the healthy individuals in Example 9, the patients with pancreatic cancer in Example 10, and the patients with renal cancer and colorectal cancer in (1), to obtain the values of the corrected first peak area %.

The results of Example 12 are shown in FIG. 9. When the specimens of the healthy individuals were compared with the specimens of patients with pancreatic cancer, renal cancer and colorectal cancer based on the values of the corrected first peak area %, which were obtained by correcting the first peak area % which increases with aging, the values of the corrected first peak area % in patients with these diseases were significantly increased as compared to healthy individuals. Since an increase in the values of the corrected first peak area % was observed as with a significant increase in the values of the first peak area % observed in Example 10, in which the specimens of the healthy individuals were compared with the specimens of patients with pancreatic cancer based on the values of the non-corrected first peak area %, it can be seen that that the difference in IgG separation pattern can be observed between the healthy individuals and cancer patients, even when the correction taking age into account was carried out.

Example 13 Evaluation of Separation of Gamma Globulin Derived from Patients with Pancreatic Cancer and Pancreatitis (1) The separation of gamma globulin was carried out in the same manner as in (2) and (3) in Example 9, except for using blood collected from patients with pancreatic cancer and pancreatitis from whom informed consent had been obtained.

(2) In each of the separation patterns obtained in (1), corresponding peaks were defined as the first peak, the second peak and the third peak, in the order of from the peak appeared at a shorter elution time after the start of the pH gradient. The area value of the first peak was divided by the total area value from the start until the end of the pH gradient, and the resulting value was defined as the first peak area %. Thereafter, the value of the corrected first peak area % was obtained in the same manner as in (2) and (3) in Example 12, and in addition, the area of the third peak was also determined, for each specimen.

The results of Example 13 are shown in FIG. 10. As can be seen in Panel (a) of FIG. 10, the values of the corrected first peak area % were significantly decreased in the specimens of patients with pancreatitis as compared to the specimens of patients with pancreatic cancer. Further, the values of the corrected first peak area % in pancreatitis patients are almost the same as those of the specimens of healthy individuals in Example 12. This reveals that the values of the corrected first peak area % do not change when healthy individuals merely contract pancreatitis. The distinguishability between pancreatic cancer and pancreatitis based on the corrected first peak area % was evaluated by the AUC value of the ROC curve, to be 0.83. On the other hand, Panel (b) of FIG. 10 shows that, when compared based on the area of the third peak, the values in the specimens of the pancreatitis patients are significantly increased as compared to the specimens of the pancreatic cancer patients. The distinguishability between the pancreatic cancer and pancreatitis based on the third peak area was evaluated by the AUC value of the ROC curve, to be 1.00. This indicates, in the case of distinguishing pancreatic lesions, that the evaluation based on the third peak area is capable of more accurately determining whether the lesions are malignant tumors or not, compared to the evaluation based on the corrected first peak area %.

Example 14 Evaluation of Separation of Gamma Globulin Derived from Smoking and Non-Smoking Healthy Individuals The separation gamma globulin was carried out in the same manner as in Example 12, except for using blood collected from smoking and non-smoking healthy individuals from whom informed consent had been obtained, and the corrected first peak area % was determined for each specimen.

The results of Example 14 are shown in FIG. 11. The values of the corrected first peak area % are significantly increased in smoking healthy individuals as compared to non-smoking healthy individuals. An increase in the values of the corrected first peak area % is the same as the tendency detected in the cancer patients in Example 12, indicating that the smoking increases the risk of being affected by cancer.

Example 15 Separation of Human-Derived Antibodies Obtained from Individuals of Different Ages, Using Different Fc-Binding Protein (FcR9_F or FcR9_V)-Immobilized Gel (1) An Fc-binding protein to which a cysteine tag was added (FcR9_V_Cys) was prepared in the same manner as in Example 3, except for using an expression vector which expresses a polypeptide having the amino acid sequence of SEQ ID NO: 17, and in which a polynucleotide encoding the polypeptide has the sequence of SEQ ID NO: 18.

(2) An FcR9_V column was prepared in the same manner as in (1) and (2) in Example 4, except for using the Fc-binding protein prepared in (1).

(3) Blood was collected from healthy individuals from whom informed consent had been obtained. The age and sex of the healthy individuals are shown below.
(Healthy individual A) 21 years old, male
(Healthy individual B) 26 years old, male
(Healthy individual C) 36 years old, male
(Healthy individual D) 47 years old, male (4) The separation pattern of gamma globulin from each individual was obtained in the same manner as in (2) and (3) in Example 8, except for using an FcR9_F column or an FcR9_V column, as the column.

(5) In each separation pattern obtained in (4), corresponding peaks were defined as the first peak, the second peak and the third peak, in the order of from the peak appeared at a shorter elution time after the start of the pH gradient. The area value of the first peak was divided by the total area value from the start until the end of the pH gradient, and the resulting value was defined as the first peak area %. Further, the value obtained by dividing the height of the first peak by the total height value of the respective peaks was defined as the first peak height %.

The results of Example 15 are shown in FIG. 12. Panel (a) of FIG. 12 is a graph showing the values of the first peak height % in the specimens of healthy individuals measured using the FcR9_F column or the FcR9_Vcolumn. It can be seen from this graph that the values of the first peak height % increase with aging. Further, the same tendency that the values of the first peak height % increase with aging, was observed, regardless of using either of two types of columns, each filled with an insoluble carrier on which one of the two types of Fc-binding proteins having different amino acid sequences was immobilized. The above results show that it is possible to detect a disease, the risk of developing a disease and/or the degree of progression of a disease, as well as the degree of progression of aging, using any Fc-binding protein, not limited to one having a particular amino acid sequence. Further, Panel (b) of FIG. 12 shows the values of the first peak area % and the first peak height % in the specimens of healthy individuals measured using the FcR9_V column. Upon comparing the area % and the height %, it can be seen that both values are increased with aging, and thus that it is possible to accurately evaluate the risk using either of these values.

INDUSTRIAL APPLICABILITY

According to the present invention, an antibody (or antibodies) can be separated based on the difference in the sugar chain structure. Further, according to one embodiment of the present invention, it is possible to detect the presence or absence of a disease, the risk of developing a disease, the degree of progression of a disease and/or the degree of progression of aging, in a subject, using as an indicator(s), a characteristic(s) of the separation pattern of the antibody.

The invention claimed is:

1. A method for detecting the presence or absence of a disease(s), the risk of developing a disease(s), the degree of progression of a disease(s), and/or the degree of progression of aging,
 wherein the method comprises the following steps (a), (b), and (c):
 (a) adding a solution containing an antibody obtained from a subject to a column filled with an insoluble carrier on which an Fc-binding protein is immobilized, to allow an antibody(ies) to be adsorbed on the carrier;
 (b) eluting the antibody(ies) adsorbed on the carrier using an eluent, to obtain data of a separation pattern of an antibody(ies); and
 (c) detecting the presence or absence of a disease(s), the risk of developing a disease(s), the degree of progression of a disease(s), and/or the degree of progression of aging, in the subject, using said data as an indicator,
 wherein the data are a characteristic(s) of the separation pattern of the antibody(ies),
 wherein the Fc-binding protein is any one of the following polypeptides (1) to (4):
 (1) a polypeptide comprising the 17th to 192nd amino acid residues of the amino acid sequence of SEQ ID NO: 1, wherein, in the 17th to 192nd amino acid residues, at least the 176th valine is substituted with phenylalanine;
 (2) a polypeptide comprising the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, the 171st phenylalanine is substituted with serine, and the 176th valine is substituted with phenylalanine;

(3) a polypeptide comprising the 17th to 192nd amino acid residues of the amino acid sequence of SEQ ID NO: 1, wherein, in the 17th to 192nd amino acid residues, at least the 27th valine is substituted with glutamic acid, the 29th phenylalanine is substituted with isoleucine, the 35th tyrosine is substituted with asparagine, the 48th glutamine is substituted with arginine, the 75th phenylalanine is substituted with leucine, the 92nd asparagine is substituted with serine, the 117th valine is substituted with glutamic acid, the 121st glutamic acid is substituted with glycine, and the 171st phenylalanine is substituted with serine; and (4) a polypeptide comprising the amino acid sequence of any one of the polypeptides (1) to (3), wherein the amino acid sequence further comprises 1 to 10 amino acid mutations at a position(s) other than the above described substitution(s).

2. The method according to claim 1, wherein the method comprises the steps (a) and (b), before performing the step (c).

3. The method according to claim 1, wherein the method comprises the step of adding an equilibrating liquid to the column to equilibrate the column, before performing the step (a).

4. The method according to claim 1, wherein the obtaining the data comprises the step of obtaining the separation pattern of the antibody(ies), and the step of extracting the characteristic(s) from the separation pattern.

5. The method according to claim 1, wherein the characteristic(s) is the peak area and/or the peak height.

6. The method according to claim 1, wherein the characteristic(s) is the peak area % and/or the peak height %.

7. The method according to claim 1, wherein the characteristic(s) is a characteristic(s) of one or more peaks selected from a first peak, a second peak, and a third peak.

8. The method according to claim 1, wherein the characteristic(s) is a characteristic(s) of the first peak.

9. The method according to claim 1, wherein the step (c) comprises the step of comparing the data with data of a separation pattern(s) of an antibody(ies) obtained from a control subject(s).

10. The method according to claim 1, wherein the disease (s) is one or more diseases selected from cancer, autoimmune diseases, infectious diseases, allergies, inflammatory diseases, cachexia, and age-related diseases.

11. The method according to claim 1, wherein the disease (s) is one or more diseases selected from pancreatic cancer, gastric cancer, breast cancer, colorectal cancer, renal cancer, rheumatism, Sjogren's syndrome, and pancreatitis.

12. The method according to claim 2, wherein the obtaining the data comprises the step of obtaining the separation pattern of the antibody(ies), and the step of extracting the characteristic(s) from the separation pattern.

13. The method according to claim 12, wherein the characteristic(s) is the peak area % and/or the peak height %.

14. The method according to claim 13, wherein the disease(s) is one or more diseases selected from cancer, autoimmune diseases, infectious diseases, allergies, inflammatory diseases, cachexia, and age-related diseases.

* * * * *